(12) United States Patent
Fairbairn et al.

(10) Patent No.: US 10,777,317 B2
(45) Date of Patent: Sep. 15, 2020

(54) AUTOMATICALLY ASSESSING AN ANATOMICAL SURFACE FEATURE AND SECURELY MANAGING INFORMATION RELATED TO THE SAME

(71) Applicant: ARANZ Healthcare Limited, Christchurch (NZ)

(72) Inventors: Christopher Keith Fairbairn, Christchurch (NZ); Michael David John Bryce, Kaiapoi (NZ); Bruce Leslie Keith Davey, Christchurch (NZ); Mark Arthur Nixon, Christchurch (NZ); Brent Stephen Robinson, Christchurch (NZ)

(73) Assignee: ARANZ Healthcare Limited, Christchurch (NZ)

( * ) Notice: Subject to any disclaimer, the term of this patent is extended or adjusted under 35 U.S.C. 154(b) by 0 days.

(21) Appl. No.: 15/974,433

(22) Filed: May 8, 2018

(65) Prior Publication Data

US 2018/0254100 A1 Sep. 6, 2018

Related U.S. Application Data

(63) Continuation of application No. 15/144,722, filed on May 2, 2016, now Pat. No. 10,013,527.

(51) Int. Cl.
*G16H 30/40* (2018.01)
*G06F 19/00* (2018.01)
(Continued)

(52) U.S. Cl.
CPC .......... *G16H 30/40* (2018.01); *G06F 19/321* (2013.01); *G06T 7/0012* (2013.01); *G06T 7/62* (2017.01);
(Continued)

(58) Field of Classification Search
CPC ... G06F 19/321; G06T 7/602; H04N 1/00244; H04N 1/00209; H04N 13/0203
See application file for complete search history.

(56) References Cited

U.S. PATENT DOCUMENTS

| 3,259,612 A | 7/1966 | Peter |
| 3,335,716 A | 8/1967 | Alt et al. |

(Continued)

FOREIGN PATENT DOCUMENTS

| DE | 2642841 | 3/1978 |
| DE | 3420588 | 12/1984 |

(Continued)

OTHER PUBLICATIONS

Afromowitz, et al., "Multispectral Imaging of Burn Wounds: A New Clinical Instrument for Evaluating Burn Depth", IEEE Transactions on Biomedical Engineering, vol. 35, No. 10, pp. 842-850; Oct. 1988.

(Continued)

*Primary Examiner* — Nam D Pham
(74) *Attorney, Agent, or Firm* — Perkins Coie LLP

(57) ABSTRACT

A facility for procuring and analyzing information about an anatomical surface feature from a caregiver that is usable to generate an assessment of the surface feature is described. The facility displays information about the surface feature used in the assessment of the surface feature. The facility obtains user input and/or data generated by an image capture device to assess the surface feature or update an existing assessment of the surface feature.

22 Claims, 18 Drawing Sheets

(51) Int. Cl.
    *G06T 7/00* (2017.01)
    *H04N 7/18* (2006.01)
    *H04N 1/00* (2006.01)
    *H04N 13/204* (2018.01)
    *G16H 15/00* (2018.01)
    *G06T 7/62* (2017.01)
    *G16H 30/20* (2018.01)

(52) U.S. Cl.
    CPC ............. *G16H 15/00* (2018.01); *G16H 30/20* (2018.01); *H04N 1/00209* (2013.01); *H04N 1/00244* (2013.01); *H04N 7/185* (2013.01); *H04N 13/204* (2018.05); *G06T 2200/24* (2013.01); *G06T 2207/10012* (2013.01); *G06T 2207/10024* (2013.01); *G06T 2207/10028* (2013.01); *G06T 2207/20092* (2013.01); *G06T 2207/30004* (2013.01)

(56) References Cited

U.S. PATENT DOCUMENTS

| | | |
|---|---|---|
| 4,090,501 A | 5/1978 | Chaitin |
| 4,170,987 A | 10/1979 | Anselmo et al. |
| 4,236,082 A | 11/1980 | Butler |
| 4,505,583 A | 3/1985 | Konomi |
| 4,515,165 A | 5/1985 | Carroll |
| 4,535,782 A | 8/1985 | Zoltan |
| 4,556,057 A | 12/1985 | Hiruma et al. |
| 4,724,480 A | 2/1988 | Hecker et al. |
| 4,736,739 A | 4/1988 | Flaton |
| 4,768,513 A | 9/1988 | Suzuki |
| 4,773,097 A | 9/1988 | Suzaki et al. |
| 4,821,117 A | 4/1989 | Sekiguchi |
| 4,839,807 A | 6/1989 | Doi et al. |
| 4,851,984 A | 7/1989 | Doi et al. |
| 4,894,547 A | 1/1990 | Leffell et al. |
| 4,930,516 A | 6/1990 | Alfano et al. |
| 4,957,114 A | 9/1990 | Zeng et al. |
| 4,979,815 A | 12/1990 | Tsikos |
| 4,996,994 A | 3/1991 | Steinhauer et al. |
| D315,901 S | 4/1991 | Knowles |
| 5,003,977 A | 4/1991 | Suzuki et al. |
| 5,016,173 A | 5/1991 | Kenet et al. |
| 5,036,853 A | 8/1991 | Jeffcoat et al. |
| 5,080,100 A | 1/1992 | Trotel |
| 5,157,461 A | 10/1992 | Page |
| 5,174,297 A | 12/1992 | Daikuzono |
| 5,241,468 A | 8/1993 | Kenet |
| 5,270,168 A | 12/1993 | Grinnell |
| 5,319,550 A | 6/1994 | Griffith |
| 5,363,854 A | 11/1994 | Martens et al. |
| 5,369,496 A | 11/1994 | Alfano et al. |
| 5,396,331 A | 3/1995 | Kitoh et al. |
| 5,408,996 A | 4/1995 | Salb |
| 5,421,337 A | 6/1995 | Richards-Kortum et al. |
| 5,515,449 A | 5/1996 | Tsuruoka et al. |
| 5,519,208 A | 5/1996 | Esparza et al. |
| 5,528,703 A | 6/1996 | Lee |
| 5,531,520 A | 7/1996 | Grimson et al. |
| 5,532,824 A | 7/1996 | Harvey et al. |
| 5,561,526 A | 10/1996 | Huber et al. |
| 5,588,428 A | 12/1996 | Smith et al. |
| 5,590,660 A | 1/1997 | MacAulay et al. |
| 5,603,318 A | 2/1997 | Heilbrun et al. |
| 5,627,907 A | 5/1997 | Gur et al. |
| 5,644,141 A | 7/1997 | Hooker et al. |
| 5,648,915 A | 7/1997 | McKinney et al. |
| 5,673,300 A | 9/1997 | Reckwerdt et al. |
| 5,689,575 A | 11/1997 | Sako et al. |
| 5,699,798 A | 12/1997 | Hochman et al. |
| 5,701,902 A | 12/1997 | Vari et al. |
| 5,717,791 A | 2/1998 | Labaere et al. |
| D393,068 S | 3/1998 | Kodama |
| 5,740,268 A | 4/1998 | Nishikawa et al. |
| 5,749,830 A | 5/1998 | Kaneko et al. |
| 5,784,162 A | 7/1998 | Cabib et al. |
| 5,791,346 A | 8/1998 | Craine et al. |
| 5,799,100 A | 8/1998 | Clarke et al. |
| 5,810,014 A | 9/1998 | Davis et al. |
| 5,836,872 A | 11/1998 | Kenet et al. |
| 5,910,972 A | 6/1999 | Ohkubo et al. |
| 5,921,937 A | 7/1999 | Davis et al. |
| 5,946,645 A | 8/1999 | Rioux et al. |
| 5,957,837 A | 9/1999 | Raab |
| 5,967,797 A | 10/1999 | Maldonado |
| 5,967,979 A | 10/1999 | Taylor et al. |
| 5,969,822 A | 10/1999 | Fright et al. |
| 5,974,165 A | 10/1999 | Giger et al. |
| 6,032,070 A | 2/2000 | Flock et al. |
| 6,081,612 A | 6/2000 | Gutkowicz-Krusin et al. |
| 6,081,739 A | 6/2000 | Lemchen |
| 6,091,995 A | 7/2000 | Ingle et al. |
| 6,101,408 A | 8/2000 | Craine et al. |
| 6,208,749 B1 | 3/2001 | Gutkowicz-Krusin et al. |
| 6,215,893 B1 | 4/2001 | Leshem et al. |
| 6,265,151 B1 | 7/2001 | Canter et al. |
| 6,266,453 B1 | 7/2001 | Hibbard et al. |
| 6,272,278 B1 | 8/2001 | Takahata et al. |
| 6,278,793 B1 | 8/2001 | Gur et al. |
| 6,307,957 B1 | 10/2001 | Gutkowicz-Krusin et al. |
| 6,324,417 B1 | 11/2001 | Cotton |
| D453,350 S | 2/2002 | Fenton |
| 6,359,513 B1 | 3/2002 | Kuo et al. |
| 6,359,612 B1 | 3/2002 | Peter |
| D455,166 S | 4/2002 | Raad |
| 6,381,026 B1 | 4/2002 | Schiff et al. |
| 6,381,488 B1 | 4/2002 | Dickey et al. |
| 6,392,744 B1 | 5/2002 | Holec |
| 6,396,270 B1 | 5/2002 | Smith |
| 6,413,212 B1 | 7/2002 | Raab |
| 6,421,463 B1 | 7/2002 | Poggio et al. |
| 6,427,022 B1 | 7/2002 | Craine et al. |
| 6,491,632 B1 | 12/2002 | Taylor |
| 6,567,682 B1 | 5/2003 | Osterweil et al. |
| 6,594,388 B1 | 7/2003 | Gindele et al. |
| 6,594,516 B1 | 7/2003 | Steckner et al. |
| 6,603,552 B1 | 8/2003 | Cline et al. |
| 6,611,617 B1 | 8/2003 | Crampton |
| 6,611,833 B1 | 8/2003 | Johnson |
| 6,631,286 B2 | 10/2003 | Pfeiffer et al. |
| 6,648,820 B1 | 11/2003 | Sarel |
| 6,671,349 B1 | 12/2003 | Griffith |
| 6,678,001 B1 | 1/2004 | Elberbaum |
| 6,690,964 B2 | 2/2004 | Bieger et al. |
| 6,715,675 B1 | 4/2004 | Rosenfeld |
| 6,754,370 B1 | 6/2004 | Hall-Holt et al. |
| 6,770,186 B2 | 8/2004 | Rosenfeld et al. |
| 6,798,571 B2 | 9/2004 | Wetzel et al. |
| 6,809,803 B1 | 10/2004 | O'Brien et al. |
| 6,810,279 B2 | 10/2004 | Mansfield et al. |
| 6,816,606 B2 | 11/2004 | Wetzel et al. |
| 6,816,847 B1 | 11/2004 | Toyama |
| 6,862,410 B2 | 3/2005 | Miyoshi |
| 6,862,542 B2 | 3/2005 | Lockhart et al. |
| 6,873,340 B2 | 3/2005 | Luby |
| 6,873,716 B1 | 3/2005 | Bowker |
| 6,879,394 B2 | 4/2005 | Amblard et al. |
| 6,907,193 B2 | 6/2005 | Kollias et al. |
| 6,915,073 B2 | 7/2005 | Seo |
| 6,922,523 B2 | 7/2005 | Merola et al. |
| 6,941,323 B1 | 9/2005 | Galperin |
| 6,961,517 B2 | 11/2005 | Merola et al. |
| 6,968,094 B1 | 11/2005 | Gallagher |
| 6,993,169 B2 | 1/2006 | Wetzel et al. |
| 7,006,223 B2 | 2/2006 | Mullani |
| 7,013,172 B2 | 3/2006 | Mansfield et al. |
| 7,015,906 B2 | 3/2006 | Olschewski et al. |
| 7,027,153 B2 | 4/2006 | Mullani |
| 7,040,536 B2 | 5/2006 | Rosenfeld |
| 7,054,674 B2 | 5/2006 | Cane et al. |
| 7,064,311 B2 | 6/2006 | Jung et al. |
| 7,068,828 B2 | 6/2006 | Kim et al. |
| 7,068,836 B1 | 6/2006 | Rubbert et al. |

(56) References Cited

U.S. PATENT DOCUMENTS

| | | |
|---|---|---|
| 7,074,509 B2 | 7/2006 | Rosenfeld et al. |
| 7,103,205 B2 | 9/2006 | Wang et al. |
| 7,106,885 B2 | 9/2006 | Osterweil et al. |
| 7,127,094 B1 | 10/2006 | Elbaum et al. |
| 7,127,280 B2 | 10/2006 | Dauga |
| 7,128,894 B1 | 10/2006 | Tannous et al. |
| 7,130,465 B2 | 10/2006 | Muenzenmayer et al. |
| 7,136,191 B2 | 11/2006 | Kaltenbach et al. |
| D533,555 S | 12/2006 | Odhe et al. |
| 7,155,049 B2 | 12/2006 | Wetzel et al. |
| 7,162,063 B1 | 1/2007 | Craine et al. |
| 7,167,243 B2 | 1/2007 | Mullani |
| 7,167,244 B2 | 1/2007 | Mullani |
| 7,181,363 B2 | 2/2007 | Ratti et al. |
| 7,194,114 B2 | 3/2007 | Schneiderman |
| 7,212,660 B2 | 5/2007 | Wetzel et al. |
| 7,227,621 B2 | 6/2007 | Lee et al. |
| 7,233,693 B2 | 6/2007 | Momma |
| D547,347 S | 7/2007 | Kim |
| 7,248,724 B2 | 7/2007 | Gutenev |
| D554,682 S | 11/2007 | Martinez |
| 7,295,226 B1 | 11/2007 | Meron et al. |
| 7,298,881 B2 | 11/2007 | Giger et al. |
| D561,804 S | 2/2008 | Asai |
| 7,347,365 B2 | 3/2008 | Rowe |
| 7,376,346 B2 | 5/2008 | Merola et al. |
| 7,400,754 B2 | 7/2008 | Jung et al. |
| 7,421,102 B2 | 9/2008 | Wetzel et al. |
| 7,426,319 B2 | 9/2008 | Takahashi |
| 7,440,597 B2 | 10/2008 | Rowe |
| 7,450,783 B2 | 11/2008 | Talapov et al. |
| 7,460,250 B2 | 12/2008 | Keightley et al. |
| 7,474,415 B2 | 1/2009 | Lin et al. |
| 7,487,063 B2 | 2/2009 | Tubic et al. |
| 7,489,799 B2 | 2/2009 | Nilsen et al. |
| 7,495,208 B2 | 2/2009 | Czarnek et al. |
| 7,496,399 B2 | 2/2009 | Maschke |
| 7,509,861 B2 | 3/2009 | Masotti et al. |
| 7,538,869 B2 | 5/2009 | Treado et al. |
| 7,545,963 B2 | 6/2009 | Rowe |
| D597,205 S | 7/2009 | Koch |
| 7,580,590 B2 | 8/2009 | Lin et al. |
| 7,581,191 B2 | 8/2009 | Rice et al. |
| 7,587,618 B2 | 9/2009 | Inui et al. |
| 7,595,878 B2 | 9/2009 | Nelson et al. |
| D603,441 S | 11/2009 | Wada |
| 7,613,335 B2 | 11/2009 | McLennan et al. |
| 7,620,211 B2 | 11/2009 | Browne et al. |
| 7,647,085 B2 | 1/2010 | Cane et al. |
| 7,668,350 B2 | 2/2010 | Rowe |
| 7,684,589 B2 | 3/2010 | Nilsen et al. |
| 7,724,379 B2 | 5/2010 | Kawasaki et al. |
| 7,729,747 B2 | 6/2010 | Stranc et al. |
| 7,735,729 B2 | 6/2010 | Rowe |
| 7,738,032 B2 | 6/2010 | Kollias et al. |
| 7,751,594 B2 | 7/2010 | Rowe et al. |
| 7,765,487 B2 | 7/2010 | Cable |
| 7,819,311 B2 | 10/2010 | Rowe et al. |
| 7,869,641 B2 | 1/2011 | Wetzel et al. |
| 7,876,948 B2 | 1/2011 | Wetzel et al. |
| 7,881,777 B2 | 2/2011 | Docherty et al. |
| 7,894,645 B2 | 2/2011 | Barsky |
| 7,912,320 B1 | 3/2011 | Minor |
| 7,912,534 B2 | 3/2011 | Grinvald et al. |
| 7,916,834 B2 | 3/2011 | Piorek et al. |
| 7,931,149 B2 | 4/2011 | Gilad et al. |
| 8,000,776 B2 | 8/2011 | Gono |
| 8,019,801 B1 | 9/2011 | Robb et al. |
| 8,026,942 B2 | 9/2011 | Payonk et al. |
| 8,071,242 B2 | 12/2011 | Rosenfeld et al. |
| 8,078,262 B2 | 12/2011 | Murphy et al. |
| 8,094,294 B2 | 1/2012 | Treado et al. |
| 8,105,233 B2 | 1/2012 | Abou El Kheir |
| D653,687 S | 2/2012 | Yu |
| 8,123,704 B2 | 2/2012 | Richards |
| 8,150,500 B2 | 4/2012 | Goldman et al. |
| 8,161,826 B1 | 4/2012 | Taylor |
| 8,165,357 B2 | 4/2012 | Rowe |
| 8,184,873 B2 | 5/2012 | Rowe et al. |
| D662,122 S | 6/2012 | Goodwin |
| 8,213,695 B2 | 7/2012 | Zouridakis |
| 8,218,873 B2 | 7/2012 | Boncyk et al. |
| 8,218,874 B2 | 7/2012 | Boncyk et al. |
| 8,224,077 B2 | 7/2012 | Boncyk et al. |
| 8,224,078 B2 | 7/2012 | Boncyk et al. |
| 8,224,079 B2 | 7/2012 | Boncyk et al. |
| 8,229,185 B2 | 7/2012 | Ennis et al. |
| 8,238,623 B2 | 8/2012 | Stephan et al. |
| 8,306,334 B2 | 11/2012 | Paschalakis et al. |
| 8,326,031 B2 | 12/2012 | Boncyk et al. |
| 8,335,351 B2 | 12/2012 | Boncyk et al. |
| 8,437,544 B2 | 5/2013 | Boncyk et al. |
| 8,457,395 B2 | 6/2013 | Boncyk et al. |
| 8,463,030 B2 | 6/2013 | Boncyk et al. |
| 8,463,031 B2 | 6/2013 | Boncyk et al. |
| 8,467,600 B2 | 6/2013 | Boncyk et al. |
| 8,467,602 B2 | 6/2013 | Boncyk et al. |
| 8,478,036 B2 | 7/2013 | Boncyk et al. |
| 8,478,037 B2 | 7/2013 | Boncyk et al. |
| 8,480,641 B2 | 7/2013 | Jacobs |
| 8,488,880 B2 | 7/2013 | Boncyk et al. |
| 8,494,264 B2 | 7/2013 | Boncyk et al. |
| 8,520,942 B2 | 8/2013 | Boncyk et al. |
| 8,533,879 B1 | 9/2013 | Taylor |
| 8,548,245 B2 | 10/2013 | Boncyk et al. |
| 8,548,278 B2 | 10/2013 | Boncyk et al. |
| 8,582,817 B2 | 11/2013 | Boncyk et al. |
| 8,588,476 B1 | 11/2013 | Spicola, Jr. |
| 8,588,527 B2 | 11/2013 | Boncyk et al. |
| D697,210 S | 1/2014 | Delaney et al. |
| 8,638,986 B2 | 1/2014 | Jiang et al. |
| 8,661,915 B2 | 3/2014 | Taylor |
| 8,712,193 B2 | 4/2014 | Boncyk et al. |
| 8,718,410 B2 | 5/2014 | Boncyk et al. |
| 8,734,342 B2 | 5/2014 | Cable |
| 8,755,053 B2 | 6/2014 | Fright et al. |
| 8,768,052 B2 | 7/2014 | Kawano |
| 8,774,463 B2 | 7/2014 | Boncyk et al. |
| 8,787,621 B2 | 7/2014 | Spicola, Sr. et al. |
| 8,787,630 B2 | 7/2014 | Rowe |
| 8,795,169 B2 | 8/2014 | Cosentino et al. |
| 8,798,368 B2 | 8/2014 | Boncyk et al. |
| 8,800,386 B2 | 8/2014 | Taylor |
| 8,814,841 B2 | 8/2014 | Hartwell |
| 8,824,738 B2 | 9/2014 | Boncyk et al. |
| 8,837,868 B2 | 9/2014 | Boncyk et al. |
| 8,842,941 B2 | 9/2014 | Boncyk et al. |
| D714,940 S | 10/2014 | Kim |
| 8,855,423 B2 | 10/2014 | Boncyk et al. |
| 8,861,859 B2 | 10/2014 | Boncyk et al. |
| 8,867,839 B2 | 10/2014 | Boncyk et al. |
| 8,873,891 B2 | 10/2014 | Boncyk et al. |
| 8,875,331 B2 | 11/2014 | Taylor |
| 8,885,983 B2 | 11/2014 | Boncyk et al. |
| 8,892,190 B2 | 11/2014 | Docherty et al. |
| 8,904,876 B2 | 12/2014 | Taylor et al. |
| 8,913,800 B2 | 12/2014 | Rowe |
| 8,923,563 B2 | 12/2014 | Boncyk et al. |
| 8,938,096 B2 | 1/2015 | Boncyk et al. |
| 8,939,918 B2 | 1/2015 | Richards |
| 8,948,459 B2 | 2/2015 | Boncyk et al. |
| 8,948,460 B2 | 2/2015 | Boncyk et al. |
| D724,216 S | 3/2015 | Gant et al. |
| 8,997,588 B2 | 4/2015 | Taylor |
| 9,014,513 B2 | 4/2015 | Boncyk et al. |
| 9,014,514 B2 | 4/2015 | Boncyk et al. |
| 9,014,515 B2 | 4/2015 | Boncyk, et al. |
| 9,020,305 B2 | 4/2015 | Boncyk et al. |
| 9,025,813 B2 | 5/2015 | Boncyk et al. |
| 9,025,814 B2 | 5/2015 | Boncyk et al. |
| 9,031,278 B2 | 5/2015 | Boncyk et al. |
| 9,036,947 B2 | 5/2015 | Boncyk et al. |
| 9,036,948 B2 | 5/2015 | Boncyk et al. |
| 9,041,810 B2 | 5/2015 | Ecker et al. |

(56) References Cited

U.S. PATENT DOCUMENTS

| | | |
|---|---|---|
| 9,110,925 B2 | 8/2015 | Boncyk et al. |
| 9,116,920 B2 | 8/2015 | Boncyk et al. |
| 9,135,355 B2 | 9/2015 | Boncyk et al. |
| 9,141,714 B2 | 9/2015 | Boncyk et al. |
| 9,148,562 B2 | 9/2015 | Boncyk et al. |
| D740,945 S | 10/2015 | Booth |
| 9,154,694 B2 | 10/2015 | Boncyk et al. |
| 9,154,695 B2 | 10/2015 | Boncyk et al. |
| 9,167,800 B2 | 10/2015 | Spicola, Jr. |
| 9,179,844 B2 | 11/2015 | Fright et al. |
| 9,186,053 B2 | 11/2015 | Viola |
| 9,224,205 B2 | 12/2015 | Tsin et al. |
| 9,235,600 B2 | 1/2016 | Boncyk et al. |
| 9,244,943 B2 | 1/2016 | Boncyk et al. |
| 9,262,440 B2 | 2/2016 | Boncyk et al. |
| 9,288,271 B2 | 3/2016 | Boncyk et al. |
| 9,311,540 B2 | 4/2016 | Ecker et al. |
| 9,311,552 B2 | 4/2016 | Boncyk et al. |
| 9,311,553 B2 | 4/2016 | Boncyk et al. |
| 9,311,554 B2 | 4/2016 | Boncyk et al. |
| 9,317,769 B2 | 4/2016 | Boncyk et al. |
| 9,324,004 B2 | 4/2016 | Boncyk et al. |
| 9,330,326 B2 | 5/2016 | Boncyk et al. |
| 9,330,327 B2 | 5/2016 | Boncyk et al. |
| 9,330,328 B2 | 5/2016 | Boncyk et al. |
| 9,330,453 B2 | 5/2016 | Soldatitsch et al. |
| 9,342,748 B2 | 5/2016 | Boncyk et al. |
| 9,377,295 B2 | 6/2016 | Fright et al. |
| 9,395,234 B2 | 7/2016 | Cosentino et al. |
| 9,399,676 B2 | 7/2016 | Schurpf et al. |
| 9,438,775 B2 | 9/2016 | Powers |
| 9,451,928 B2 | 9/2016 | Falco et al. |
| 9,861,285 B2 | 1/2018 | Fright et al. |
| 9,955,910 B2 | 5/2018 | Fright et al. |
| 2002/0054297 A1 | 5/2002 | Lee et al. |
| 2002/0149585 A1 | 10/2002 | Kacyra et al. |
| 2002/0197600 A1 | 12/2002 | Maione et al. |
| 2003/0004405 A1 | 1/2003 | Townsend et al. |
| 2003/0006770 A1 | 1/2003 | Smith |
| 2003/0031383 A1 | 2/2003 | Gooch |
| 2003/0036751 A1 | 2/2003 | Anderson et al. |
| 2003/0085908 A1 | 5/2003 | Luby |
| 2003/0164841 A1 | 9/2003 | Myers |
| 2003/0164875 A1 | 9/2003 | Myers |
| 2003/0229514 A2 | 12/2003 | Brown |
| 2003/0231793 A1 | 12/2003 | Crampton |
| 2004/0014165 A1 | 1/2004 | Keidar et al. |
| 2004/0059199 A1 | 3/2004 | Thomas et al. |
| 2004/0080497 A1 | 4/2004 | Enmei |
| 2004/0117343 A1 | 6/2004 | Johnson |
| 2004/0136579 A1 | 7/2004 | Gutenev |
| 2004/0146290 A1 | 7/2004 | Kollias et al. |
| 2004/0201694 A1 | 10/2004 | Gartstein et al. |
| 2004/0225222 A1 | 11/2004 | Zeng et al. |
| 2004/0264749 A1 | 12/2004 | Skladnev et al. |
| 2005/0012817 A1 | 1/2005 | Hampapur et al. |
| 2005/0027567 A1 | 2/2005 | Taha |
| 2005/0033142 A1 | 2/2005 | Madden et al. |
| 2005/0084176 A1 | 4/2005 | Talapov et al. |
| 2005/0094262 A1 | 5/2005 | Spediacci et al. |
| 2005/0111757 A1 | 5/2005 | Brackett et al. |
| 2005/0154276 A1 | 7/2005 | Barducci et al. |
| 2005/0190988 A1 | 9/2005 | Feron |
| 2005/0237384 A1 | 10/2005 | Jess et al. |
| 2005/0259281 A1 | 11/2005 | Boust |
| 2005/0273011 A1 | 12/2005 | Hattery et al. |
| 2005/0273267 A1 | 12/2005 | Maione |
| 2006/0008178 A1 | 1/2006 | Seeger et al. |
| 2006/0012802 A1 | 1/2006 | Shirley |
| 2006/0036135 A1 | 2/2006 | Kern |
| 2006/0036156 A1 | 2/2006 | Lachaine et al. |
| 2006/0044546 A1 | 3/2006 | Lewin et al. |
| 2006/0055943 A1 | 3/2006 | Kawasaki et al. |
| 2006/0058665 A1 | 3/2006 | Chapman |
| 2006/0072122 A1 | 4/2006 | Hu et al. |
| 2006/0073132 A1 | 4/2006 | Congote |
| 2006/0089553 A1 | 4/2006 | Cotton |
| 2006/0098876 A1 | 5/2006 | Buscema |
| 2006/0135953 A1 | 6/2006 | Kania et al. |
| 2006/0151601 A1 | 7/2006 | Rosenfeld |
| 2006/0204072 A1 | 9/2006 | Wetzel et al. |
| 2006/0210132 A1 | 9/2006 | Christiansen et al. |
| 2006/0222263 A1 | 10/2006 | Carlson |
| 2006/0268148 A1 | 11/2006 | Kollias et al. |
| 2006/0269125 A1 | 11/2006 | Kalevo et al. |
| 2006/0293613 A1 | 12/2006 | Fatehi et al. |
| 2007/0065009 A1 | 3/2007 | Ni et al. |
| 2007/0097381 A1 | 5/2007 | Tobiason et al. |
| 2007/0125390 A1 | 6/2007 | Afriat et al. |
| 2007/0129602 A1 | 6/2007 | Bettesh et al. |
| 2007/0229850 A1 | 10/2007 | Herber |
| 2007/0273894 A1 | 11/2007 | Johnson |
| 2007/0276195 A1 | 11/2007 | Xu et al. |
| 2007/0276309 A1 | 11/2007 | Xu et al. |
| 2008/0006282 A1 | 1/2008 | Sukovic |
| 2008/0021329 A1 | 1/2008 | Wood et al. |
| 2008/0045807 A1 | 2/2008 | Psota et al. |
| 2008/0088704 A1 | 4/2008 | Wendelken et al. |
| 2008/0098322 A1 | 4/2008 | Champion et al. |
| 2008/0126478 A1 | 5/2008 | Ferguson et al. |
| 2008/0165357 A1 | 7/2008 | Stem |
| 2008/0232679 A1 | 9/2008 | Hahn |
| 2008/0246759 A1 | 10/2008 | Summers |
| 2008/0275315 A1 | 11/2008 | Oka et al. |
| 2008/0285056 A1 | 11/2008 | Blayvas |
| 2008/0312642 A1 | 12/2008 | Kania et al. |
| 2008/0312643 A1 | 12/2008 | Kania et al. |
| 2009/0116712 A1 | 5/2009 | Al-Moosawi et al. |
| 2009/0118720 A1 | 5/2009 | Black et al. |
| 2009/0213213 A1 | 8/2009 | Fright et al. |
| 2009/0221874 A1 | 9/2009 | Vinther |
| 2009/0225333 A1 | 9/2009 | Bendall |
| 2009/0234313 A1 | 9/2009 | Mullejeans et al. |
| 2010/0004564 A1 | 1/2010 | Jendle |
| 2010/0020164 A1 | 1/2010 | Perrault |
| 2010/0091104 A1 | 4/2010 | Sprigle et al. |
| 2010/0111387 A1 | 5/2010 | Christiansen, II et al. |
| 2010/0121201 A1 | 5/2010 | Papaionnou |
| 2010/0149551 A1 | 6/2010 | Malinkevich |
| 2010/0156921 A1 | 6/2010 | McLennan et al. |
| 2010/0191126 A1 | 7/2010 | Al-Moosawi et al. |
| 2010/0278312 A1 | 11/2010 | Ortiz |
| 2011/0125028 A1 | 5/2011 | Wood et al. |
| 2011/0190637 A1 | 8/2011 | Knobel et al. |
| 2012/0035469 A1 | 2/2012 | Whelan et al. |
| 2012/0059266 A1 | 3/2012 | Davis et al. |
| 2012/0078088 A1 | 3/2012 | Whitestone et al. |
| 2012/0078113 A1 | 3/2012 | Whitestone et al. |
| 2012/0253200 A1 | 10/2012 | Stolka et al. |
| 2012/0265236 A1 | 10/2012 | Wesselmann |
| 2012/0275668 A1 | 11/2012 | Chou et al. |
| 2013/0051651 A1 | 2/2013 | Leary et al. |
| 2013/0137991 A1 | 5/2013 | Fright et al. |
| 2013/0335545 A1 | 12/2013 | Darling |
| 2014/0048687 A1 | 2/2014 | Drzymala et al. |
| 2014/0088402 A1 | 3/2014 | Xu |
| 2014/0354830 A1 | 12/2014 | Schafer et al. |
| 2015/0077517 A1 | 3/2015 | Powers |
| 2015/0089994 A1 | 4/2015 | Richards |
| 2015/0142462 A1* | 5/2015 | Vaidya .............. G06F 19/3418 705/2 |
| 2015/0150457 A1 | 6/2015 | Wu et al. |
| 2015/0214993 A1 | 7/2015 | Huang |
| 2015/0250416 A1 | 9/2015 | LaPlante et al. |
| 2015/0265236 A1 | 9/2015 | Garner et al. |
| 2015/0270734 A1 | 9/2015 | Davison et al. |
| 2016/0157725 A1 | 6/2016 | Munoz |
| 2016/0206205 A1 | 7/2016 | Wu et al. |
| 2016/0259992 A1 | 9/2016 | Knodt et al. |
| 2016/0261133 A1 | 9/2016 | Wang |
| 2016/0262659 A1 | 9/2016 | Fright et al. |
| 2016/0284084 A1 | 9/2016 | Gurcan et al. |
| 2016/0338594 A1 | 11/2016 | Spahn et al. |
| 2017/0079577 A1 | 3/2017 | Fright et al. |

(56) References Cited

U.S. PATENT DOCUMENTS

| | | |
|---|---|---|
| 2017/0084024 A1 | 3/2017 | Gurevich |
| 2017/0086940 A1 | 3/2017 | Nakamura |
| 2017/0127196 A1 | 5/2017 | Blum et al. |
| 2018/0132726 A1 | 5/2018 | Dickie et al. |
| 2018/0214071 A1 | 8/2018 | Fright et al. |
| 2018/0271378 A1 | 9/2018 | Fright et al. |

FOREIGN PATENT DOCUMENTS

| | | |
|---|---|---|
| DE | 4120074 | 1/1992 |
| EP | 119660 | 9/1984 |
| EP | 355221 | 2/1990 |
| EP | 552526 | 7/1993 |
| EP | 650694 | 5/1995 |
| EP | 1210906 | 6/2002 |
| EP | 1248237 | 10/2002 |
| EP | 1351036 | 10/2003 |
| EP | 1584405 | 10/2005 |
| EP | 1611543 | 1/2006 |
| EP | 1946567 | 7/2008 |
| FR | 2570206 | 3/1986 |
| NZ | 293713 | 9/1997 |
| WO | WO2000003210 | 1/2000 |
| WO | WO2000030337 | 5/2000 |
| WO | WO2002065069 | 6/2002 |
| WO | WO2002001143 | 7/2002 |
| WO | WO2002093450 | 11/2002 |
| WO | WO2004092874 | 10/2004 |
| WO | WO2004095372 | 11/2004 |
| WO | WO2005033620 | 4/2005 |
| WO | 2006078902 A2 | 7/2006 |
| WO | 2007029038 A1 | 3/2007 |
| WO | 2007043899 A1 | 4/2007 |
| WO | 2007059780 A1 | 5/2007 |
| WO | 2008033010 A1 | 3/2008 |
| WO | 2008039539 A2 | 4/2008 |
| WO | 2008048424 A2 | 4/2008 |
| WO | 2008057056 A1 | 5/2008 |
| WO | 2008071414 A1 | 6/2008 |
| WO | 2008080385 A1 | 7/2008 |
| WO | 2009046218 A2 | 4/2009 |
| WO | 2010048960 A1 | 5/2010 |
| WO | WO2012146720 | 11/2012 |
| WO | 2016199134 A1 | 12/2016 |
| WO | 2018185560 A2 | 10/2018 |

OTHER PUBLICATIONS

Ahroni, JH et al "Reliability of computerized wound surface area determinations" Wounds: A Compendium of Clinical Research and Practice, No. 4, (1992) 133-137.

Anderson, R., et al. "The Optics of Human Skin", The Journal of Investigative Dermatology, vol. 77, No. 1, pp. 13-19; Jul. 1981.

Armstrong, DG et al "Diabetic foot ulcers: prevention, diagnosis and classification" Am Fam Physician Mar. 15, 1998; 57 (6) :1325-32, 1337-8.

Bale, S, Harding K, Leaper D. An Introduction to Wounds. Emap Healthcare Ltd 2000.

Beaumont, E et al "RN Technology Scorecard: Wound Care Science at the Crossroads" American Journal of Nursing Dec. 1998 98(12):16-18, 20-21.

Bergstrom, N, Bennett MA, Carlson CE. Treatment of Pressure Ulcers: Clinical Practice Guideline No. 15. Rockville, MD: U.S. Department of Health and Human Services. Public Health Service, Agency for Health Care Policy and Research 1994: 95-0652: [O].

Berriss 1997: Automatic Quantitative Analysis of Healing Skin Wounds using Colour Digital Image Processing: William Paul Berriss, Stephen John Sangwine [E].

Binder, et al., "Application of an artificial neural network in epiluminescence microscopy pattern analysis of pigmented skin lesions: a pilot study", British Journal of Dermatology 130; pp. 460-465; 1994.

Bland, JM et al "Measurement error and correlation coefficients" BMJ Jul. 6, 1996; 313 (7048) :41-2.

Bland, JM et al "Measurement error" BMJ Jun. 29, 1996; 312 (7047) :1654.

Bohannon Richard; Barbara A Pfaller Documentation of Wound Surface Area from Tracings of Wound Perimeters [E].

Bostock, et al, Toward a neural network based system for skin cancer diagnosis; IEEE Conference on Artificial neural Networks, ISBN: 0-85296-573-7, pp. 215-219, May 1993.

BPG2005: Assessment and Management of Foot Ulcers for People with Diabetes: Nursing Best Practice Guidelines, Toronto, Ontario [E], Mar. 2013.

Briggs Corporation: Managed care making photo documentation a wound care standard. Wound care solutions product catalog 1997.

Brown, G "Reporting outcomes for Stage IV pressure ulcer healing: a proposal" Adv Skin Wound Care (2000)13:277-83.

Callieri 2003: Callieri M, Cignoni P, Pingi P, Scopigno R. Derma: Monitoring the evolution of skin lesions with a 3D system, VMV 2003. 8th International Fall Workshop, Vision, Modeling, and Visualization 2003, Nov. 19-21, 2003, Munich, Germany [E].

Campana: XML-based synchronization of mobile medical devices [E], 2002, 2 Pages.

Cascinelli, N., et al. "Results obtained by using a computerized image analysis system designed as an aid to diagnosis of cutaneous melanoma", Melanoma Research, vol. 2, pp. 163-170, 1992.

Collins, C et al "The Role of Ultrasound in Lower Extremity Wound Management" International Journal of Lower Extremity Wounds (2002) 1: 229-235.

Daubechies, I., "The Wavelet Transform, Time-Frequency Localization and Signal Analysis", IEEE Trans Inform Theory, vol. 36, No. 5, pp. 961-1005; Sep. 1990.

De Vet, HC et al "Current challenges in clinimetrics" J Clin Epidemiol Dec. (2003); 56 (12) :1137-41.

Debray, M., Couturier P, Greuillet F, Hohn C, Banerjee S, Gavazzi G, Franco A. "A preliminary study of the feasibility of wound telecare for the elderly." Journal of Telemedicine & Telecare 2001: 7(6): 353-8. [A].

Duff, et al. (2003), Loftus Hills A, Morrell C 2000 Clinical. Guidelines for the management of venous leg ulcers: Implementation Guide. Royal College of Nursing; 2000: 001 (213): 1-48. [E].

Ercal, F., "Detection of Skin Tumor Boundaries in Color Images", IEEE Transactions of Medical Imaging, vol. 12, No. 3, pp. 624-627, Sep. 1993.

Ercal, F., et al. "Neural Network Diagnosis of Malignant Melanoma From Color Images", IEEE Transactions of Biomedical Engineering, vol. 41, No. 9, pp. 837-845, Sep. 1994.

Ferrell, B "Pressure ulcers. Assessment of healing" Clin Geriatr Med (1997)13:575-87.

Fitzpatrick, R et al "Evaluating patient-based outcome measures for use in clinical trials" Health Technol Assess (1998); 2 (14): i-iv, 1-74.

Flahr, et al. 2005: Clinimetrics and Wound Science [E].

Flanagan, M. "Improving accuracy of wound measurement in clinical practice" Ostomy Wound Manage Oct. 2003 49(10):28-40.

Flanagan, M., "Wound measurement: can it help us to monitor progression to healing?" JWound Care May 12, 2003(5):189-94.

Gilman, T "Wound outcomes: the utility of surface measures" Int J Low Extrem Wounds Sep. 2004; 3 (3) :125-32.

Goldman, RJ "The patientcom, 1 year later" Adv Skin Wound Care Nov.-Dec. 2002; 15 (6) :254, 256.

Goldman, RJ et al "More than one way to measure a wound: An overview of tools and techniques" Adv Skin Wound Care (2002) 15:236-45.

Golston, et al. "Automatic Detection of Irregular Borders in Malanoma and Other Skin Tumors", Computerized Medical Imaging and Graphics, vol. 16, No. 3, pp. 199-203, 1992.

Graaf, R., et al. "Optical properties of human dermis in vitro and in vivo", Applied Optics, vol. 32, No. 4, pp. 435-447, Feb. 1, 1993.

Greene, A., "Computer image analysis in the diagnosis of melanoma", Journal of the American Academy of Dermatology; vol. 31, No. 6, pp. 958-964, 1994.

(56) References Cited

OTHER PUBLICATIONS

Griffin, JW et al "A comparison of photographic and transparency-based methods for measuring wound surface area" Phys Ther Feb. 1993; 73 (2) :117-22.

Hansen 1997: Wound Status Evaluation Using Color Image Processing Gary: L. Hansen, Ephraim M. Sparrow, Jaydeep Y. Kokate, Keith J. Leland, and Paul A. Iaizzo [E].

Hayes 2003: Hayes S, Dodds, S. Digital photography in wound care. Nursing Times 2003:9(42):48-9. [A].

Herbin, et al, Color Quantitation Through Image Processing in Dermatology; IEEE Transaction on Medical Imaging, vol. 9, Issue 3, pp. 262-269, Sep. 1990.

Hibbs, P "The economics of pressure ulcer prevention" Decubitus Aug. 1988; 1 (3) :32-8.

Houghton 2000: Houghton PE, Kincaid CB, Campbell KE, Woodbury MG, Keast DH. Photographic assessment of the appearance of chronic pressure and leg ulcers. Ostomy Wound management 2000: 46(4): 20-6, 28-30. [A].

Huang, C., et al."Border irregularity: atypical moles versus melanoma", Eur J Dermatol, vol. 6, pp. 270-273, Jun. 1996.

Iakovou, D. et al., "Integrated sensors for robotic laser welding," Proceedings of the Third International WLT-Conference on Lasers in Manufacturing, Jun. 2005, pp. 1-6.

International Search Report and Written Opinion for International Application No. PCT/US2004/028445 filed Sep. 1, 2004.

Johnson, JD (1995) Using ulcer surface area and volume to document wound size.

Jones, et al, An Instrument to Measure the Dimension of Skin Wounds; IEEE Transaction on Biomedical Engineering, ISSN: 0018-9294; vol. 42, Issue 5, pp. 464-470, May 1995.

Jones, TD "Improving the Precision of Leg Ulcer Area Measurement with Active Contour Models", PhD Thesis (1999) http://www.comp.glam.ac.uklpages/staff/tjones/ThesisOL/Title.Htm.

Jones, TD et al "An active contour model for measuring the area of leg ulcers" IEEE Trans Med Imaging Dec. (2000) 19(12):1202-10.

Kenet, R. et al."Clinical Diagnosis of Pigmented Lesions Using Digital Epiluminescence Microscopy", Arch Dermatol, vol. 129, pp. 157-174; Feb. 1993.

Kloth, LC et al "A Randomized Controlled Clinical Trial to Evaluate the Effects of Noncontact Normothermic Wound Therapy on Chronic Full-thickness Pressure Ulcers" Advances in Skin & Wound Care Nov./Dec. 15, 2002(6):270-276.

Koren, et al, Interactive Wavelet Processing and Techniques Applied to Digital Mammography; IEEE Conference Proceedings, ISBN: 0-7803-3192-3; vol. 3, pp. 1415-1418, May 1996.

Kovesi, P., "Image Features From Phase Congruency", University of Western Australia, pp. 1-30; Technical Report 9/4, Revised Jun. 1995.

Krouskop, TA et al "A noncontact wound measurement system" J Rehabil Res Dev May-Jun. 2002 39(3):337-45.

Kundin 1989: Kudin JI. A new way to size up a wound. American Journal of Nursing 1989: (2):206-7.

Langemo, DK et al "Comparison of 2 Wound Volume Measurement Methods" Advances in Skin & Wound Care Jul./Aug. 2001, vol. 14(4), 190-196.

Langemo, DK et al "Two- dimensional wound measurement: comparison of 4 techniques" Advances in Wound Care Nov.-Dec. 11, 1998(7):337-43.

Laughton, C et al "A comparison of four methods of obtaining a negative impression of the foot" J Am Podiatr Med Assoc May 2002; 92 (5) :261-8.

Lee, et al, A Multi-stage Segmentation Method for Images of Skin Lesions; IEEE Conference Proceedings on Communication, Computers, and Signal Processing, ISBN 0-7803-2553-2, pp. 602-605, May 1995.

Levoy, et al. "The Digital Michelangelo Project: 3D Scanning of Large Statues," ACM, 2000.

Lewis 1997: Lewis P, McCann R, Hidalgo P, Gorman M. Use of store and forward technology for vascular nursing teleconsultation service. Journal of Vascular Nursing 1997. 15(4): 116-23. [A].

Lewis, JS, Achilefu S, Garbow JR, Laforest R, Welch MJ., Small animal imaging. current technology and perspectives for oncological imaging, Radiation Sciences, Washington University School of Medicine, Saint Louis, MO, USA, Eur J Cancer. Nov. 2002;38(16):2173-88.

Li, D. 2004, Database design and implementation for wound measurement system. Biophotonics, 2004: 42-43. [E].

Lorimer, K "Continuity through best practice: design and implementation of a nurse-led community leg-ulcer service" Can J Nurs Res Jun. 2004 36(2):105-12.

Lowery et al., "Technical Overview of a Web-based Telemedicine System for Wound Assessment," Advances in Skin & Wound Care, Jul./Aug. 2002, pp. 165-169, vol. 15, No. 4.

Lowson, S., "The safe practitioner: Getting the record straight: the need for accurate documentation," J Wound Care, Dec. 2004, vol. 13, No. 10, [retrieved on Dec. 17, 2004). Retrieved from the Internet: <URL: http://www.journalofwoundcare.com/nav?page=jowc.article&resource=I455125>, 2 pages.

Lucas, C., "Pressure ulcer surface area measurement using instant full-scale photography and transparency tracings," Advances in Skin & Wound Care, Jan./Feb. 2002, [retrieved on Jul. 28, 2006]. Retrieved from the Internet: <URL: http://www.findarticles.com/p/articles/mi_qa3977/is_200201 /ai_n904 . . . >, 7 pages.

Lunt, M.J., "Review of duplex and colour Doppler imaging of lower-limb arteries and veins," World Wide Wounds, 2000, [retrieved on Apr. 17, 2005]. Retrieved from the Internet: <URL: http://www.worldwidewounds.com/2000/sept/Michael-Lunt/Dopple . . . >, 6 pages.

Maglogiannis et al., "A system for the acquisition of reproducible digital skin lesions images," Technol and Health Care, 2003, pp. 425-441, vol. 11.

Malian et al., "MEDPHOS: A New Photogrammetric System for Medical Measurement," 2004, Commission V, WG V/3, 6 pages.

Mallat, S., et al. "Characterization of signals from multiscale edges", IEEE Trans Patt and Mech Int'l; 14:710-732; 1992.

Marchesini, R., et al. "In vivo Spectrophotometric Evaluation of Neoplastic and Non-Neoplastic Skin Pigmented Lesions. III. CCD Camera-Based Reflectance Imaging", Photochemistry and Photobiology, vol. 62, No. 1, pp. 151-154; 1995.

Marjanovic et al., "Measurement of the volume of a leg ulcer using a laser scanner," Physiol. Meas., 1998, pp. 535-543, vol. 19.

Mastronjcola et al., "Burn Depth Assessment Using a Tri-stimulus Colorimeter," Wounds—ISSN: !044-7946, Sep. 2005, pp. 255-258, vol. 17, No. 9.

McCardle, J., "Visitrak: wound measurement as an aid to making treatment decisions," The Diabetic Foot, Winter 2005, [retrieved on Mar. 30, 2008). Retrieved from the Internet: <URL: http://findarticles.com/p/articles/mi_mOMDQ/is_ 4_8/ai_n16043804/print>, 4 pages.

Menzies, S., "The Morphologic Criteria of the Pseudopod in Surface Microscopy", Arch Dermatol, vol. 131, pp. 436-440, Apr. 1995.

Nachbar, et al., "The ABCD rule of dermatology", Journal of the American Academy of Dermatology, vol. 3, No. 4, pp. 551-559, Apr. 1994.

National Pressure Ulcer Advisory Panel, "FAQ: Photography for pressure ulcer documentation," 1 1 P56, 4 pages .

National Pressure Ulcer Advisory Panel, Position Statement, 1998, [retrieved on Jan. 6, 2005]. Retrieved from the Internet: <URL: http://www.npuap.org/>, 2 pages (Pressure Ulcer Healing Chart attached, 2 pages).

Oduncu et al., "Analysis of Skin Wound Images Using Digital Color Image Processing: A Preliminary Communication," Lower Extremity Wounds, 2004, pp. 151-156, vol. 3, No. 3.

Pages, Jordi, et al., "Plane-to-plane positioning from image-based visual serving and structured light," Proceedings of 2004 IEEE/RSJ International Conference on Intelligent Robots and Systems, Sep. 28-Oct. 2, 2004, pp. 1004-1009.

Patete et al., "A non-invasive, three-dimensional, diagnostic laser imaging system for accurate wound analysis," Physiol. Meas., 1996, pp. 71-79, vol. 17.

Pehamberger, H., et al. "In vivo epiluminescence microscopy of pigmented skin lesions. I. Pattern analysis of pigmented skin lesions", Journal of American Academy of Dermatology, vol. 17, No. 4, pp. 571-583, Oct. 1987.

(56) References Cited

OTHER PUBLICATIONS

Plassman, et al. "Problems of Assessing Wound Size," Would healing Research Unit, University of Wales College of Medicine, Cardiff CF4 4XN, Wales, UK (1993) (Unpublished).
Plassmann et al., "MAVIS: a non-invasive instrument to measure area and volume of wounds," Medical Engineering & Physics, 1998, pp. 332-338, vol. 20.
Plassmann, P., "Recording Wounds—Documenting Woundcare," Medical Computing Group, 1998, pp. 1-31.
Romanelli et al., "Technological Advances in Wound Bed Measurements," Wounds, 2002, pp. 58-66, vol. 14, No. 2, [retrieved on Apr. 8, 2005]. Retrieved from the Internet: <URL: http:/lwww.medscape.com/viewarticle/430900 _print>, 8 pages.
Russell, L., "The importance of wound documentation & classification," British J Nursing, 1999, pp. 1342-1354, vol. 8, No. 20.
Salcido, R., "The Future of Wound Measurement," Advances in Skin & Wound Care, Mar./Apr. 2003, pp. 54, 56, vol. 13, No. 2.
Salmhofer, et al., "Wound teleconsultation in patients with chronic leg ulcers," 2005.
Sani-Kick et al., "Recording and Transmission of Digital Wound Images with the Help of a Mobile Device," 2002, 2 pages.
Santamaria et al., "The effectiveness of digital imaging and remote expert wound consultation on healing rates in chronic lower leg ulcers in the Kimberley region of Western Australia," Primary Intention, May 2004, pp. 62-70, vol. 12, No. 2.
Schindewolf, et al. "Comparison of classification rates for conventional and dermatoscopic images of malignant and benign melanocytic lesions using computerized colour image analysis", Eur J Dermatol, vol. 3, No. 4, pp. 299-303, May 1993.
Schindewolf, T., et al. "Classification of Melanocytic Lesions with Color and Texture Analysis Using Digital Image Processing", The International Academy of Cytology, Analytical and Quantitative Cytology and Histology, vol. 15, No. 1, pp. 1-11, Feb. 1993.
Schindewolf, T., et al. "Evaluation of different image acquisition techniques for a computer vision system in the diagnosis of malignant melanoma", Journal of the American Academy of Dermatology, vol. 31, No. 1, pp. 33-41, Jul. 1994.
Schultz et al., "Wound bed preparation: a systematic approach to wound management," Wound Repair and Regeneration, Mar./Apr. 2003, p. SI-S28, vol. 1 1, No. 2, Supplement.
Sheehan et al., "Percent Change in Wound Area of Diabetic Foot Ulcers Over a 4-Week Period is a Robust Predictor of Complete Healing in a 12-Week Prospective Trial," Diabetes Care, Jun. 2003, pp. 1879-1882, vol. 26, No. 6.
Sheng, Chao, Brian W. Pogue, Hamid Dehghani, Julia A. O'Hara, P. J. Hoopes, Numerical light dosimetry in murine tissue: analysis of tumor curvature and angle of incidence effects upon fluence in the tissue, Proc. SPIE, vol. 4952, 39 (2003), DOI:10.1117/12.474081, Online Publication Date: Jul. 28, 2003.
Smith & Nephew, "Leg ulcer guidelines: a pocket guide for practice," National Guideline Clearinghouse, U.S. Dept of Health & Human Services, 2002, [retrieved on Jan. 10, 2012]. Retrieved from the Internet: <URL: http://guidelines.gov/content.aspx?id=9830 &search=Pressure+Ulcer>, 17 pages.
Smith & Nephew, "Visitrak Wound Measurement Device," Wound Management, [retrieved on Apr. 7, 2005]. Retrieved from the Internet: <URL: http://wound.smith-nephew.com/us/node.asp?NodeId=3 I 20>, 7 pages.
Smith & Nephew, "Guidelines for the Management of Leg Ulcers in Ireland" www.smith-nephew.com.
Smith et al., "Three-Dimensional Laser Imaging System for Measuring Wound Geometry," Lasers in Surgery and Medicine, 1998, pp. 87-93, vol. 23.
Sober, et al., "Computerized Digital Image Analysis: An Aid for Melanoma Diagnosis", The Journal of Dermatology, vol. 21, pp. 885-890, 1994.
Solomon et al., "The use of video image analysis for the measurement of venous ulcers,". British J Dermatology, 1995, pp. 565-570, vol. I 33.
Steiner, A., "In vivo epiluminescence microscopy of pigmented skin lesions. II. Diagnosis of small pigmented skin lesions and early detection of malignant melanoma", Journal of the American Academy of Dermatology, vol. 17, No. 4, pp. 584-591; Oct. 1987.
Stoecker, et al. "Automatic Detection of Asymmetry in Skin Tumors", Computerized Medical Imaging and Graphics, vol. 16, No. 3, pp. 191-197, 1992.
Takiwaki, et al., "A rudimentary system for automatic discrimination among basic skin lesions on the basis of color analysis of video images", Journal of the American Academy of Dermatology, vol. 32, No. 4, pp. 600-604, Apr. 1995.
Tellez, R., "Managed Care Making Photo Documentation a Wound Care Standard," Wound Care, 1997, [retrieved on Aug. 29, 2005]. Retrieved from the Internet: <URL: http://woundcare.org/newsvol2n4/arl.htm>, 2 pages.
Thawer et al., "A Comparison of Computer-Assisted and Manual Wound Size Measurement," Ostomy Wound Management, Oct. 2002, pp. 46-53, vol. 48, No. IO.
Umbaugh et al., "Automatic Color Segmentation Algorithms with Application to Skin Tumor Feature Identification", IEEE Engineering in Medicine and Biology, pp. 75-82, Sep. 1993.
Umbaugh, et al., "An Automatic Color Segmentation Algorithm with Application to Identification of Skin Tumor Borders", Computerized Medical Imaging and Graphics, vol. 16, No. 3, pp. 227-235, May-Jun. 1992.
Umbaugh, et al., "Automatic Color Segmentation of Images with Application to Detection of Variegated Coloring in Skin Tumors", IEEE Engineering in Medicine and Biology Magazine, Dec. 1989, pp. 43-52.
Vermolen et al., "A simplified model for growth factor induced healing of circular wounds," 2005, pp. 1-15.
Voigt, H., et al. "Topodermatographic Image Analysis for Melanoma Screening and the Quantitative Assessment of Tumor Dimension Parameters of the Skin", Cancer, vol. 75, No. 4, Feb. 15, 1995.
Walker, N, Rogers A, Birchall N, Norton R, MacMahon S. Leg ulcers in New Zealand: age at onset, recurrence and provision of care in an urban population. NZ Med J; 2002; 115(1156):286-9.
Walker, N, Vandal A, Holden K, Rogers A, Birchall N, Norton R, Triggs C, MacMahon S. Does capture-recapture analysis provide more reliable estimates of the incidence and prevalence of leg ulcers in the community? Aust NZJ Public Health 2002; 26(5):451-5.
Walker, N., Rodgers A, Birchall N, Norton R, MacMahon S. The occurrence of leg ulcers in Auckland: results of a population-based study. NZ Med J; 2002: 115 (1151): 159-162.
Wallenstein et al., "Statistical analysis of wound-healing rates for pressure ulcers," Amer J Surgery, Jul. 2004 (Supplement), pp. 73S-78S, vol. 188.
Wilbright, W.A., The Use of Telemedicine in the Management of Diabetes-Related Foot Ulceration: A Pilot Study, Advances in Skin & Wound Care, Jun. 2004, [retrieved on Jul. 28, 2006]. Retrieved from the Internet: <URL: http://www.findarticles.com/p/articles/mi_qa3977/is_200406/ai_n942 . . . >, 6 pages.
Wild et al., "Wound healing analysis and measurement by means of colour segmentation," ETRS Poster Presentation V28, Sep. 15, 2005, V28-I 7, 1 page.
Williams, C., "The Verge Videometer wound measurement package," British J Nursing, Feb./Mar. 2000, pp. 237-239, vol. 9, No. 4.
Woodbury et al., Pressure ulcer assessment instruments: a critical appraisal, Ostomy Wound Management, May 1999, pp. 48-50, 53-55, vol. 45, No. 5, [retrieved on Dec. 8, 2005]. Retrieved from the Internet: <URL: http://gateway.ut.ovid.com.ezproxy.otago.ac.nzigw2/ovidweb.cgi>, 2 pages.
Woodbury, M.G., "Development, Validity, Reliability, and Responsiveness of a New Leg Ulcer Measurement Tool," Advances in Skin & Wound Care, May 2004, [retrieved on Jul. 28, 2006]. Retrieved from the Internet:.
Zhao, et al, The Classification of the Depth of Burn Injury Using Hybrid Neural Network; IEEE Conference on Engineering in Medicine and Biology Society, ISBN 0-7803-2475-7; vol. 1, pp. 815-816, Sep. 1995.
Zimmet, "Venous Leg Ulcers: Evaluation and Management," American College of Phlebology. 1998.

(56) References Cited

OTHER PUBLICATIONS

Zuijlen, PPM., Angeles AP, Suijker MH, Kreis RW, Middelkoop E. Reliability and Accuracy of Techniques for Surface Area Measurements of Wounds and Scars. The International Journal of Lower Extremity Wounds 2004: 3(1) 7-11.

Thali, M.J., et al. "Optical 3D surface digitizing in forensic medicine: 3D documentation of skin and bone injuries." Forensic Science International. 2003.

Ahn et al., "Advances in Wound Photography and Assessment Methods," Advances in Skin & Wound Care, Feb. 2008, pp. 85-93.

Bolton, L., "Re Measuring Wound Length, Width, and Area: Which Technique?" Letters, Advances in Skin & Wound Care, pp. 450-452, vol. 21, No. 10.

Briers, J.D., "Laser speckle contast imaging for measuring blood flow," Optica Applicata, 2007, pp. 139-152, vol. XXXVII, No. 1-2.

Cardinal et al., "Early healing rates and wound area measurements are reliable predictors of later complete wound closure," Wound Rep. Reg., 2008, pp. 19-22, vol. 16.

Cardinal et al., "Wound shape geometry measurements correlate to eventual wound healing," Wound Rep. Reg., 2009, pp. 173-178, vol. 17.

Cleator et al., "Mobile wound care: Transforming care through technology," Rehab & Community Care Medicine, Winter 2008, pp. 14-15.

De Vet, H C., et al., "When to use agreement versus reliability measures", J Clin Eoidemiol 59 (10), (Oct. 2006), 1033-9.

Duckworth et al., "A Clinically Affordable Non-Contact Wound Measurement Device," 2007, pp. 1-3.

Fette, A.M., "A clinimetric analysis of wound measurement tools," World Wide Wounds, 2006, [retrieved on Jul. 26, 2006]. Retrieved from the Internet: <URL: http://www.worldwidewounds.com/2006/January/Fette/Clinimetric-Ana . . . >, 6 pages.

Gethin et al., "Wound Measurement: the contribution to practice," EWMA Journal, 2007, pp. 26-28, vol. 7, No. 1.

Haghpanah et al., "Reliability of Electronic Versus Manual Wound Measurement Techniques," Arch Phys Med Rehabil, Oct. 2006, pp. 1396-1402, vol. 87.

HSA Global, "Mobile Wound Care", Marketing material (2009).

International Search Report and Written Opinion dated Jan. 23, 2019, International Application No. PCT/IB2018/000447, 20 pages.

International Search Report and Written Opinion dated Jul. 2, 2019, International Application No. PCT/IB2018/001572, 17 pages.

International Search Report and Written Opinion dated Mar. 1, 2007, International Application No. PCT/NZ2006/000262, 12 pages.

Kecelj-Leskovec et al., "Measurement of venous leg ulcers with a laser-based three-dimensional method: Comparison to computer planimetry with photography," Wound Rep Reg, 2007, pp. 767-771, vol. 15.

Khashram et al., "Effect of TNP on the microbiology of venous leg ulcers: a pilot study," J Wound Care, Apr. 2009, pp. 164-167, vol. 18, No. 4.

Korber et al., "Three-dimensional documentation of wound healing: First results of a new objective method for measurement," JDDG, Oct. 2006, (Band 4), pp. 848-854.

Lakovou, D. et al., "Integrated sensors for robotic laser welding," Proceedings of the Third International WLT-Conference on Lasers in Manufacturing, Jun. 2005, pp. 1-6.

Langemo et al., "Measuring Wound Length, Width, and Area: Which Technique?", Advances in Skin & Wound Care, Jan. 2008, pp. 42-45, vol. 21, No. I.

Liu et al., "Wound measurement by curvature maps: a feasibility study," Physiol. Meas., 2006, pp. I 107-1123, vol. 27.

Molnar et al., "Use of Standardized, Quantitative Digital Photography in a Multicenter Web-based Study," 2009, ePlasty, pp. 19-26, vol. 9.

Payne, C., "Cost benefit comparison of plaster casts and optical scans of the foot for the manufacture of foot orthoses," AJPM, 2007, pp. 29-31, vol. 41, No. 2.

Rogers et al., "Measuring Wounds: Which Stick to Use?", Podiatry Management, Aug. 2008, pp. 85-90.

Salcido, R., "Pressure Ulcers and Wound Care," Physical Medicine and Rehabilitation, eMedicine, 2006, [retrieved on]. Retrieved from the Internet: <URL: http://www.emedicine.com/pmr/topic 179.htrn>, 25 pages.

Shaw et al., "An Evaluation of Three Wound Measurement Techniques in Diabetic Foot Wounds," Diabetes Care, 2007, [retrieved on Mar. 30, 2008]. Retrieved from the Internet: <URL: http://care.diabetesjournals.org/cgi/content/full/30/ I 0/2641 ?ck=nck>, 5 pages.

Treuillet et al., "Three-Dimensional Assessment of Skin Wounds Using a Standard Digital Camera," IEEE Transactions on Medical Imaging, May 2009, pp. 752-762, vol. 28, No. 5.

Wang et al., "A comparison of digital planimetry and transparency tracing based methods for measuring diabetic cutaneous ulcer surface area," Zhongguo Xiu Fu Chong Jian Wai Ke Za Zhi, May 2008, pp. 563-566, vol. 22, No. 5, [retrieved on Sep. 15, 2009]. Retrieved from the Internet: <URL: http://www.ncbi.nlm.nih.gov/pu bmed/ I 8630436?ordinalpos= I &itool=E . . . >, I page.

Wendelken et al., "Key Insights on Mapping Wounds With Ultrasound," Podiatry Today, Jul. 2008, [retrieved on Jul. 14, 2008]. Retrieved from the Internet: <URL: http://www.podiatrytoday.com/article/5831>, 5 pages.

* cited by examiner

AUTOMATICALLY ASSESSING AN ANATOMICAL SURFACE FEATURE AND SECURELY MANAGING INFORMATION RELATED TO THE SAME

CROSS-REFERENCE TO RELATED APPLICATION

This application is a continuation of U.S. patent application Ser. No. 15/144,722, filed May 2, 2016, now U.S. Pat. No. 10,013,527, the disclosure of which is incorporated herein by reference in its entirety.

TECHNICAL FIELD

The present technology is generally related to devices, systems, and methods for assessing anatomical surface features and securely managing information related to the same.

BACKGROUND

Various techniques have been used to monitor anatomical surface features, such as wounds, ulcers, sores, lesions, tumors etc. (herein referred to collectively as "surface features") both within hospitals and outside hospitals (e.g. domiciliary-based care, primary care facilities, hospice and palliative care facilities, etc.). Wounds, for example, are typically concave and up to about 250 millimeters across. Manual techniques are often labor-intensive and require examination and contact by skilled personnel. Such measurements may be inaccurate, and there may be significant variation between measurements made by different personnel. Further, these approaches may not preserve any visual record for review by an expert or for subsequent comparison. Accordingly, there is a need for improved systems for assessing surface features.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Overview

Described herein is a software facility for automatically assessing an anatomical surface feature ("the facility"), such as a wound, and for managing information related to assessed anatomical surface features across a range of patients and institutions. While the following discussion liberally employs the term "wound" to refer to the anatomical surface feature(s) being assessed, those skilled in the art will appreciate that the facility may be straightforwardly applied to anatomical surface features of other types, such as ulcers, sores, lesions, tumors, bruises, burns, moles, psoriasis, keloids, skin cancers, erythema, cellulitis, and the like. Similarly, a wide variety of users may use the facility, including doctors, nurses, technologists, or any other caregiver of the patient.

As used herein, the terms "computer" and "computing device" generally refer to devices that have a processor and non-transitory memory, as well as any data processor or any device capable of communicating with a network. Data processors include programmable general-purpose or special-purpose microprocessors, programmable controllers, application-specific integrated circuits (ASICs), programming logic devices (PLDs), system on chip (SOC) or system on module (SOM) ("SOC/SOM"), an ARM class CPU with embedded Linux or Android operating system or the like, or a combination of such devices. Computer-executable instructions may be stored in memory, such as random access memory (RAM), read-only memory (ROM), flash memory, or the like, or a combination of such components. Computer-executable instructions may also be stored in one or more storage devices, such as magnetic or optical-based disks, flash memory devices, or any other type of non-volatile storage medium or non-transitory medium for data. Computer-executable instructions may include one or more program modules, which include routines, programs, objects, components, data structures, and so on that perform particular tasks or implement particular abstract data types.

Anatomical Surface Feature Assessment

Figure 1:
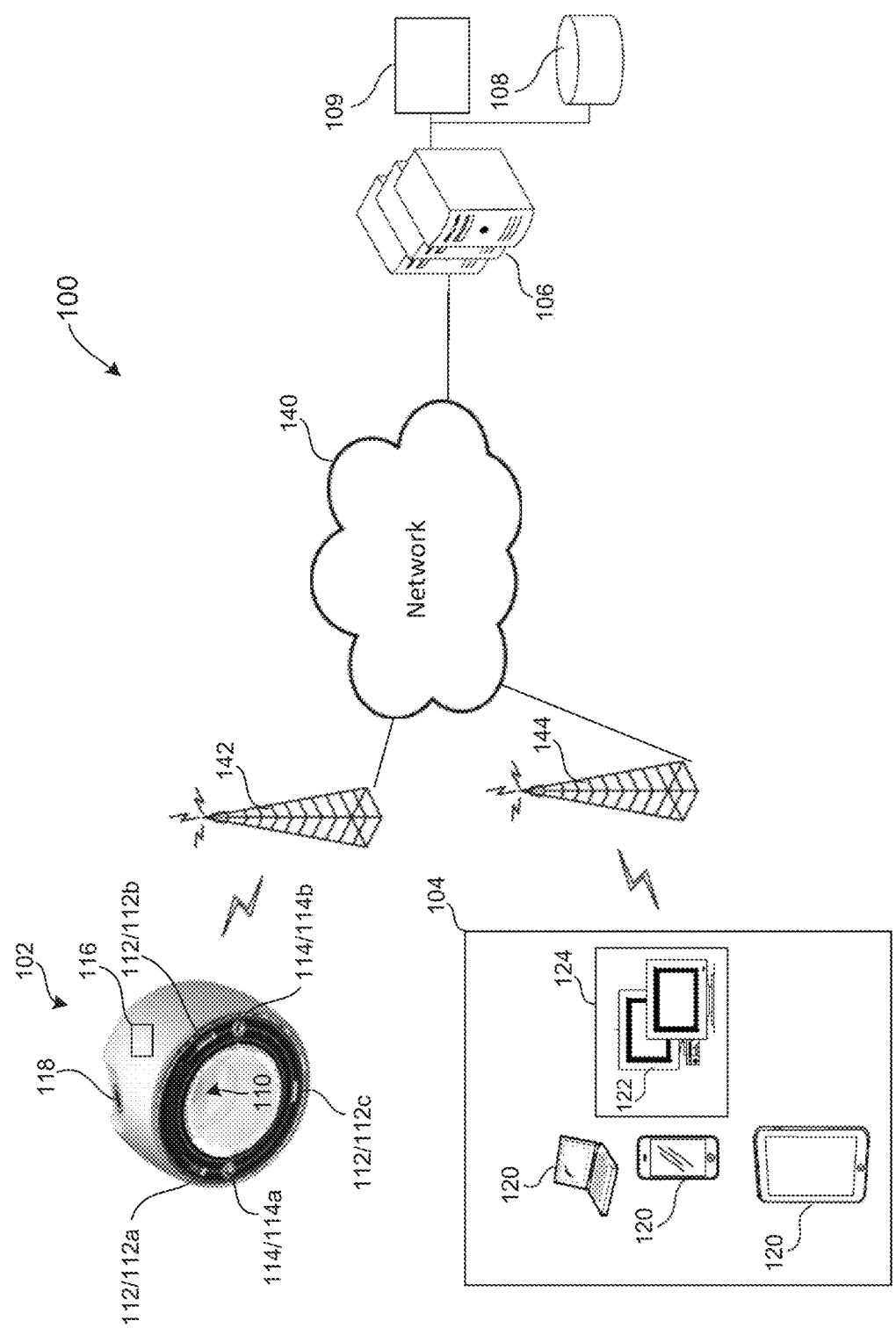
FIG. 1 is a diagram showing some of the components typically incorporated in at least some of the computer systems and other devices on which the facility executes.

FIG. 1 is a block diagram showing a sample environment having multiple components n which the facility executes.

The environment 100 may include one or more capture devices 102, one or more personal computing devices 104, one or more server computers 106, and one or more persistent storage devices 108. The capture device 102 and the personal computing device 104 communicate (wirelessly or through a wired connection) with the server computer 106 through a network 140 such as, for example, a Local Area Network (LAN), a Wide Area Network (WAN), and/or the Internet. In the embodiment shown in FIG. 1, the capture device 102 does not communicate directly with the personal computing device 104. For example, the capture device 102 may communicate wirelessly with a first base station or access point 142 using a wireless mobile telephone standard, such as the Global System for Mobile Communication (GSM), or another wireless standard, such as IEEE 802.11, and the first base station or access point 142 communicates with the server computer 106 via the network 140. Likewise, the computing device 104 may communicate wirelessly with a second base station or access point 144 using a wireless mobile telephone standard, such as the Global System for Mobile Communication (GSM), or another wireless standard, such as IEEE 802.11, and the second base station or access point 144 communicates with the server computer 106 via the network 140. As such, confidential patient data generated by the capture device 102 is only temporarily stored locally, or not at all, and instead is permanently stored at the storage device 108 associated with the server computer 106. The facility can be practiced on any of the computing devices disclosed herein (e.g., one or more personal computing devices 104, one or more server computers 106, etc.), and may include an interface module that generates graphical user interfaces (GUIs) to allow users to access the facility (as described in greater detail below with reference to FIGS. 3-12D).

The personal computing device 104 can include one or more portable computing devices 120 (e.g., a smart phone, a laptop, a tablet, etc.) and/or one or more desktop computing devices 122. During data capture with the capture device 102 at the point-of-care, the personal computing device 104 may also be present (i.e., in the same treatment room), or the personal computing device 104 may be remote (i.e., outside of the treatment room but in the same treatment facility, outside of the treatment facility, etc.). The desktop computing devices 122, if utilized, are typically associated with a particular property, e.g., a medical treatment center 124 (e.g., a hospital, a doctor's office, a clinic, etc.). The portable computing devices 120 and desktop computing devices 124 communicate with each other and the server computer 106 through networks including, for example, the Internet. In some instances the portable computing devices 120 and desktop computing devices 122 may communicate with each other through other wireless protocols, such as near field or Bluetooth.

The capture device 102 is a handheld, portable imaging device that includes one or more sensing devices for generating data characterizing the wound ("wound data") at the point-of-care. In the embodiment shown in FIG. 1, the capture device 102 includes an image sensor 110 (e.g., a digital camera), a depth sensor 112 (also known as a "range imager"), and a computing device 116 (shown schematically) in communication with the image sensor 110 and the depth sensor 112. The computing device 116 is also in wireless communication with the server computer 106 (e.g., via the network 140). The image sensor 110 is configured to generate image data of the wound (e.g., pixels containing RGB color data), and the depth sensor 112 is configured to generate depth data characterizing the depth or topography of the wound. For example, in some embodiments the depth sensor 112 is a structured light device configured to emit structured light (e.g., one or more lasers, DLP projectors, film projectors, etc. where the emitted light may be infra-red, visible, ultraviolet, etc.) in a predetermined arrangement toward the wound. In such embodiments, for example, the depth sensor 112 may comprise three laser elements (labeled 112a-112c) spaced apart around a circumference of the capture device 102. The laser elements 112a-112c have a fixed positional relationship with respect to one another, and also with respect to the image sensor 110. Together the laser elements 112a-112c can be configured to create a structured light pattern (e.g., a laser point(s), a laser fan(s), etc.) In other embodiments, the depth sensor 112 can include other suitable devices for range imaging, such as an ultrasonic sensor, a stereo camera, a plenoptic camera, a time-of-flight camera, etc.

The capture device 102 also includes a rechargeable power source and an actuator 118 (e.g., a button, a switch, etc.) for initiating data capture. When a user presses the button 118, the computing device 116 simultaneously activates both the image sensor 110 and the depth sensor 112 to generate both the image data and the depth data. The computing device 116 then communicates the image data and the depth data to the remote server computer 106 for further processing by the facility. In some embodiments, the computing device 116 wirelessly communicates with the server computer 106 (e.g., over a network). Such a cordless arrangement can be advantageous as it allows the user greater freedom of movement with the capture device 102, which can be especially beneficial when trying to access certain anatomical locations. Also, the absence of a cord reduces the surface area available at the point-of-care on which bacteria and/or other unwanted microorganisms may bind and travel. In some embodiments, the capture device 102 may be permanently cordless (i.e., no input port), and in other embodiments, the capture device 102 may be configured to detachably receive an electronic connector, such as a power cord or a USB cord. The computing device 116 may automatically transfer the captured data to the remote server computer 106 (e.g., over the network 140) at the moment the data is captured. In certain embodiments, however, the computing device 116 may not be in communication with the network 140; in such scenarios, the captured data may be temporarily stored in the volatile and/or non-volatile memory of the capture device 102 for later transfer to the server computer 106.

The capture device 102 may include additional features for enhancing data collection of the wound, such as one or more light sources 114 (e.g., a light emitting diode (LED), an incandescent light source, an ultraviolet light source, etc.) for illuminating the wound before or during data capture, an indicator (not shown) configured to provide a visual and/or audio signal (e.g., images, text, lights, etc.) to the user, a thermal camera, a video camera, and/or one or more input/output devices (e.g., a microphone, a speaker, a port for communicating electrically with external components, such as a power source, the personal computing device 104, etc.). In some embodiments, the capture device 102 is configured for wireless charging, e.g., via a dock or cradle (not shown). In such embodiments, the charging cradle may also serve as an access point for the network 140. As discussed in greater detail below with reference to FIGS. 5A-5B, the capture device 102 and/or image sensor 110 may also be configured to capture images of barcodes and/or QR codes displayed on the computing device 104, such as a barcode and/or a QR code that enable the capture device 102 to connect to the network 140.

Those skilled in the art will appreciate that the capture device 102 may have other configurations than that shown in FIG. 1. For example, although the image sensor 110, depth sensor 112, and computing device 116 are shown as part of a single component and/or within the same housing, in other embodiments, any or all of the of the image sensor 110, the depth sensor 112, and the computing device 116 can be separate components. Likewise, in some embodiments, the capture device 102 does not include separate image and depth sensors, and instead includes a stereo camera that is configured to generate both image data and depth data. Additional details regarding suitable capture devices 102 and methods of use can be found in U.S. Pat. No. 8,755,053, filed May 11, 2009 and U.S. Pat. No. 9,179,844, filed Nov. 27, 2012, both of which are incorporated herein by reference in their entireties.

As discussed above, the facility may include an interface module that generates graphical user interfaces (GUIs) to allow users to access the facility. The interface module also provides application programming interfaces (APIs) to enable communication and interfacing with the facility. APIs may be used by other applications, web portals, or distributed system components to use the system. For example, an application operating on a personal computing device may use an API to interface with system servers and receive capture data from the system. The API may utilize, for example, Representational State Transfer (REST) architecture and Simple Object Access Protocol (SOAP) protocols.

Figure 2:
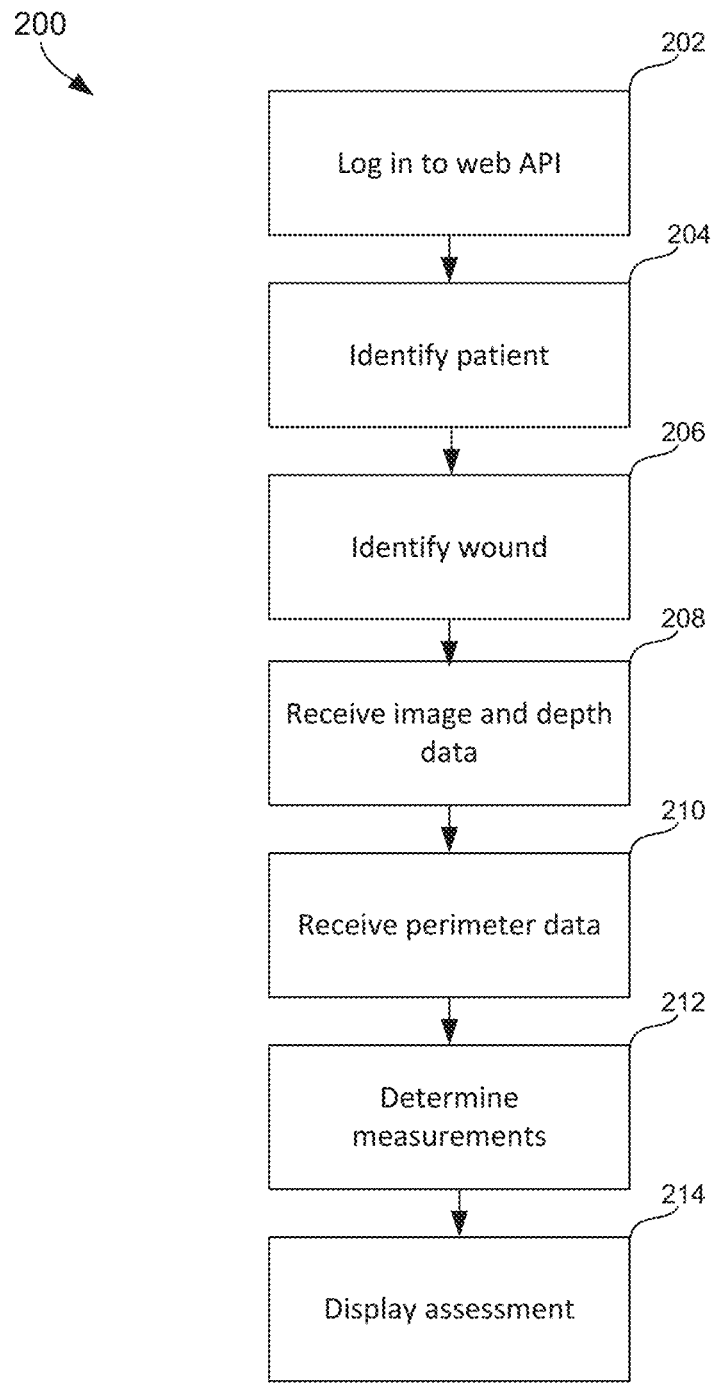
FIG. 2 is a flow diagram showing steps typically performed by the facility to automatically assess an anatomical surface feature of a human patient.

FIG. 2 is a flow diagram showing steps typically performed by the facility to assess a wound of a patient and/or manage data (including meta data) related to the wound. At step 202, the facility provides a display that solicits the user to enter login information (e.g., a username and password) to permit the user to access the facility and/or the storage device 108 (see, for example, FIG. 3). At step 204, the facility solicits the user to identify the patient having a wound needing assessment (see, for example, FIG. 4). If the patient is new to the database, the facility enables the user to create a new data structure (or profile) for the patient, and a new data structure (or profile) for the wound that is associated with the patient's profile. If the patient already exists in the database, then the facility displays a unique identifier for the patient or otherwise enables the user to access the already-existing patient profile. Once the facility has identified the patient, the facility solicits the user to identify the wound to be reviewed and/or assessed (see, for example, FIG. 5A). If the wound has not yet been entered into the patient profile, the facility enables the user to create a new data structure (or profile) for the wound and associates that data structure with the already-existing patient profile. If the wound already exists in the patient profile, then the facility displays a unique identifier for the particular wound or otherwise enables the user to access the already-existing wound profile. At some point after the facility has identified the corresponding patient and wound profile, the facility receives new image data, new depth data, and new outline data characterizing the wound and assigns the new data to the wound profile (steps 208-210). As shown at steps 212- 214, the facility then analyzes this data to determine one or more wound measurements (such as wound area and wound volume), and displays the wound measurements to the user.

Those skilled in the art will appreciate that the steps shown in FIG. 2 may be altered in a variety of ways. For example, the order of the steps may be rearranged, sub steps may be performed in parallel, shown steps may be omitted, other steps may be included, etc.

FIGS. 3-12D contain sample displays presented by the facility in some embodiments in performing portions of the method shown in FIG. 2. In the following discussion, the user interacts with the facility through a web-based interface, and thus all tasks or modules of the facility are performed at a remote server computer (such as server computer 106). However, the facility can also be practiced in distributed computing environments, where tasks or modules of the facility are performed by multiple remote processing devices (such as the personal computing device 104 and the server computer 106), which are linked through a communications network, such as a Local Area Network ("LAN"), Wide Area Network ("WAN"), or the Internet. For example, those skilled in the relevant art will recognize that portions of the facility may reside on a server computer, while corresponding portions reside on a remote or personal computing device. In such a distributed computing environment, program modules or subroutines may be located in and executed on both local and remote memory storage devices. Aspects of the facility described herein may be stored or distributed on tangible, non-transitory computer-readable media, including magnetic and optically readable and removable computer discs, stored in firmware in chips (e.g., EEPROM chips). Alternatively, aspects of the facility may be distributed electronically over the Internet or over other networks (including wireless networks).

Figure 3:
FIG. 3 is a display diagram showing a sample display typically presented by the facility to permit the user to enter a username and password to access the facility.

To begin a wound assessment, a caregiver may first provide a username and password to gain access to the interface module. For example, FIG. 3 is a display diagram showing a sample display 300 typically presented by the facility that solicits the user to enter a username and password to access the programs and data stored at the storage device 108. As shown in FIG. 3, the display 300 includes a username field 302 and a password field 304.

Figure 4:
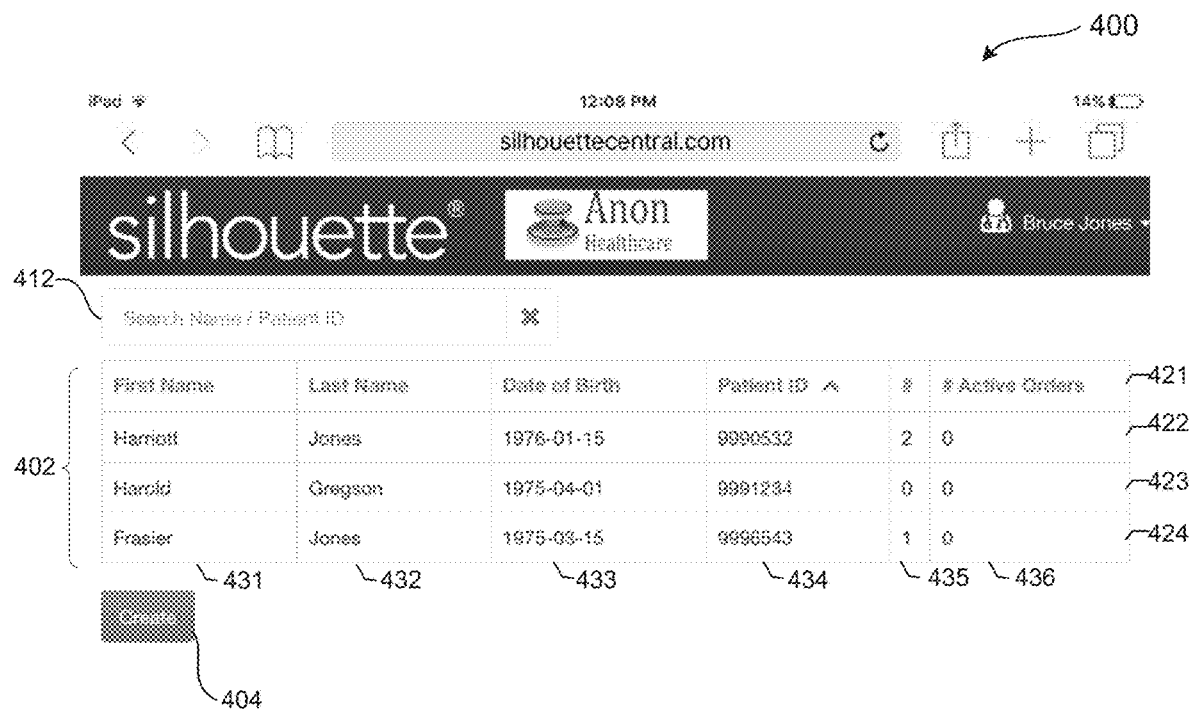
FIG. 4 is a display diagram showing a sample display typically presented by the facility to permit the user to select an existing patient profile and/or create a new patient profile.

FIG. 4 is a display diagram showing a sample display 400 typically presented by the facility to permit the user to select an existing patient profile and/or create a new patient profile. The display 400 includes a generic search field 412 for searching for a particular patient by name, birthday, unique identifier, and/or assessment date. The display 400 further includes a control 404 to create a new patient profile. The display 400 may also include an existing patient table 402 listing existing patient profiles in rows 421-424. Each row is divided into the following sortable and/or filterable columns: a first name column 431 containing the first name of an already-assessed patient, a last name column 432 containing the last name of an already-assessed patient, a date-of-birth column 433 containing the date of birth of an already-assessed patient, a patient ID column 434 containing the patient ID of an already-assessed patient, a "#" column 435 containing the number of wound assessments performed on the already-assessed patient, and a number of active orders column 436 containing indicated the number of orders for new assessments that are currently pending. Orders for new assessments might come, for example, from an Electronic Medical Records (EMR) system attached to the server computer 106. In the sample display 400 shown in FIG. 4, row 421 indicates that patient Harriet Jones has at least one wound that has been previously assessed by the facility, and that Harriet Jones' date of birth is Jan. 15, 1976 and patient ID is 9990532, and that Harriet Jones has two assessments completed but no orders for another assessment. (It will be appreciated that the patient information used in the displays and examples herein are fictitious.) While the contents of patient table 400 are included to pose a comprehensible example, those skilled in the art will appreciate that the facility can use a patient table having columns corresponding to different and/or a larger number of attributes, as well as a larger number of rows to accommodate additional patients. Attributes that may be used include, for example, number of wounds actively being monitored, date and/or time of the most recent assessment, date and/or time of the first assessment, name or other identifier of the caregiver that gave the last assessment, etc. For a variety of reasons, certain values may be omitted from the patient table.

Figure 5A:
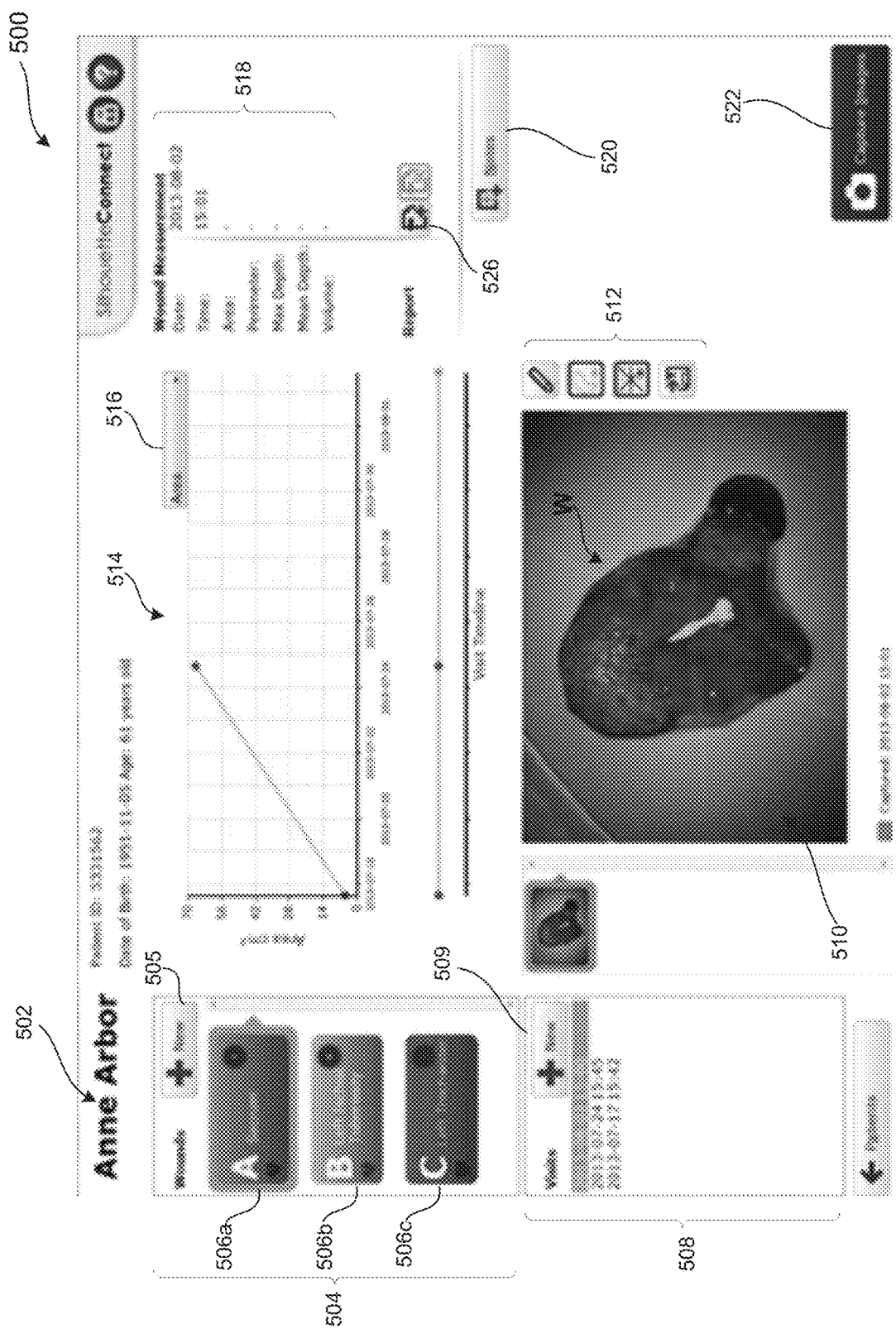
FIG. 5A is a display diagram showing a sample display typically presented by the facility to display surface feature information for a selected patient and enable the user to capture additional images of the surface feature.

When the user clicks on one of the rows 421-424 of already-assessed patients listed (i.e., to selected a particular patient profile), the facility displays additional information on the selected patient. For example, FIG. 5A is a display diagram showing a sample wound information display 500 typically presented by the facility for review of wounds already being monitored or assessed by the facility. Display 500 includes a patient identifier 502, a wound identifier area 504, a visit area 508, an image area 510, an analytics area 514, and a wound measurement area 518. The wound identifier area 504 includes a button 505 for adding a new wound profile, as well as buttons 506a-506c, each of which correspond to a wound of the patient that is being monitored. As shown in FIG. 5A, the buttons 506a-506c identify the corresponding monitored wound by anatomical reference. For example, button A refers to a wound found at or near the sacrum of the patient. The buttons 506a-506c may also be color-coded. When the user selects one of the buttons 506a-506c, the facility displays information related to the selected wound, such as the most recent wound image 510, analytics 514 showing progress of the selected wound, and wound measurements 518. The sample display 500 of FIG. 5A shows a display after a user has selected wound A (by clicking on button 506a).

The visit area 508 displays the dates and times of previous assessments for the selected wound. The user may select a particular visit to review the wound assessment from the selected visit. The visit area includes a button 509 for creating a new visit for the selected wound. The wound image area 510 displays an image of the wound W. The default image is that from the most recent assessment (or visit), although the user can view wound images from earlier visits by selecting the particular visit in the visit area 508. The wound image area 510 can include buttons 512 that allow the user to manipulate the displayed image. In some embodiments, the wound image area 510 may include display a three-dimensional model of the wound. The wound measurement area 518 displays one or more wound measurements, such as wound area, wound volume, wound outline, the maximum depth of the wound, the minimum depth of the wound, etc. In display 500, the wound measurement area 518 is blank, as the user has not yet generated new capture data. As shown in the display 500' of FIG. 9 (discussed below), the facility will display the measurements once the user has captured new wound data. The analytics area 514 displays additional information to the user based on the facility's analysis of the wound measurements over time. For example, the analytics area 514 of the display 500 shows a graph plotting the measured area of wound A over time. The graph indicates that wound A has been previously assessed two times, and that the area of the wound increased between those assessments. The analytics area 514 may include a button 516 that, when selected, displays a drop-down menu of wound measurement options that may be plotted over time and displayed for the user.

Figure 5B:
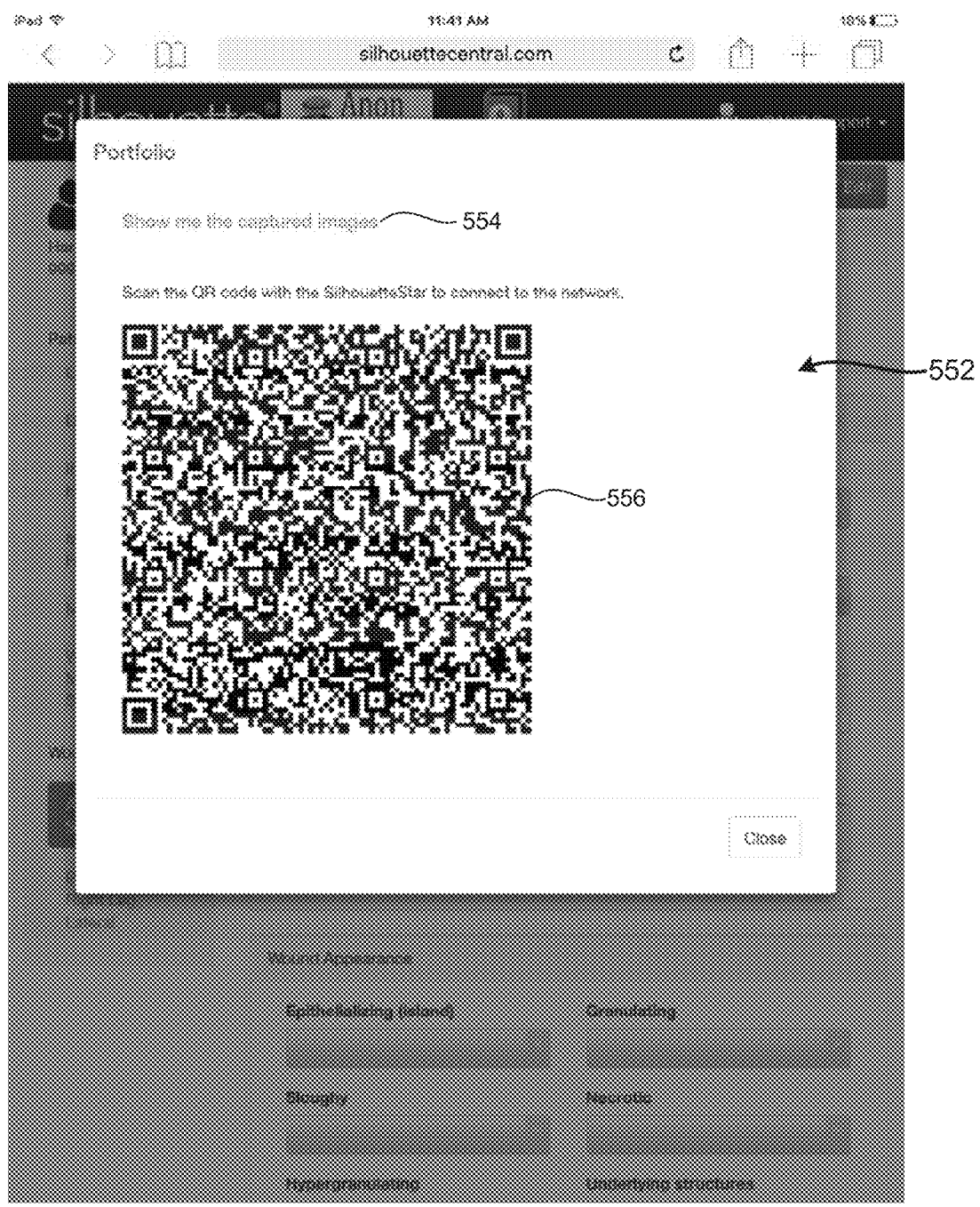
FIG. 5B is a display diagram showing a sample display typically presented by the facility to enable the user to automatically couple a particular capture device to the facility.

In some embodiments, the facility may enable the user to couple (i.e., pair, associate, etc.) the capture device 102 to the facility so that the capture device 102 may automatically send captured data to a specific patient profile in the storage device 108 that is accessible by the facility for processing. In FIG. 5A, for example, the display 500 includes a button 522 that, when selected by the user, causes the facility to dynamically generate coupling information. FIG. 5B is a display diagram showing a sample display 550 having coupling information 556 that may be presented by the facility to the user. In FIG. 5B, the coupling information 556 is displayed as a QR code. In other embodiments, however, the coupling information 556 can have other configurations, such as a bar code, text that the user may enter into an input element of the capture device 102, etc. The user may scan or otherwise detect the coupling information 556 with the capture device 102 (e.g., via the image sensor 110 of the capture device 102) to automatically place the capture device 102 in communication with a particular patient profile in the storage device 108. The coupling information 556, for example, can include a network identifier and password (e.g., an SSID and SSID password), an Internet address (e.g., the URL for the interface module), and a patient identifier for directing the capture device 102 to the particular patient profile at the storage device 108. Once the capture device 102 is wirelessly coupled to the server computer 106 and/or storage device 108, the user can position the capture device 102 near the wound being assessed and begin capturing wound data. Each time the user actuates the actuator 118 (FIG. 1) on the capture device 102, the capture device 102 automatically populates the patient profile at the storage device 108 with a new data set. The user may select button 554 to view the captured images and/or data. Each new data set may be displayed by the facility as an unassigned image button, as discussed in greater detail below with reference to FIG. 6.

It will be appreciated that the coupling information 556 may be encrypted to protect the patient's confidential information. For example, in the embodiment shown in FIG. 5B, the QR code 556 is encrypted such that a screen shot of display 552 will not provide the coupling information and/or provide access to a recipient of the screen shot.

The present technology includes additional methods for coupling the capture device 102 to the facility. For example, in some embodiments, some or all of the coupling information may be received from an identifier on the patient, such as a patient wristband. As another example, in some embodiments the facility may display a list of capture devices 102 available on the network 140 (FIG. 1) (e.g., a plurality of capture devices 102 may be dispersed amongst different examination rooms in a medical treatment center, and at least a portion of those devices may be coupled to the same wireless network). The facility may display (e.g., via the interface module) each of the capture devices 102 available, and enable the user to select the appropriate capture device 102 for pairing. The facility may then solicit the user to input a patient identifier and/or additional information for connecting the capture device 102 to the facility and/or server computer 106. In yet another embodiment, the capture device 102 may be placed in direct communication with the personal computing device 104 (e.g., via a USB cord), and the user may input pairing information into a local program executing on the personal computing device 104 and/or a web-based interface executing on the remote server computer 106.

Figure 6:
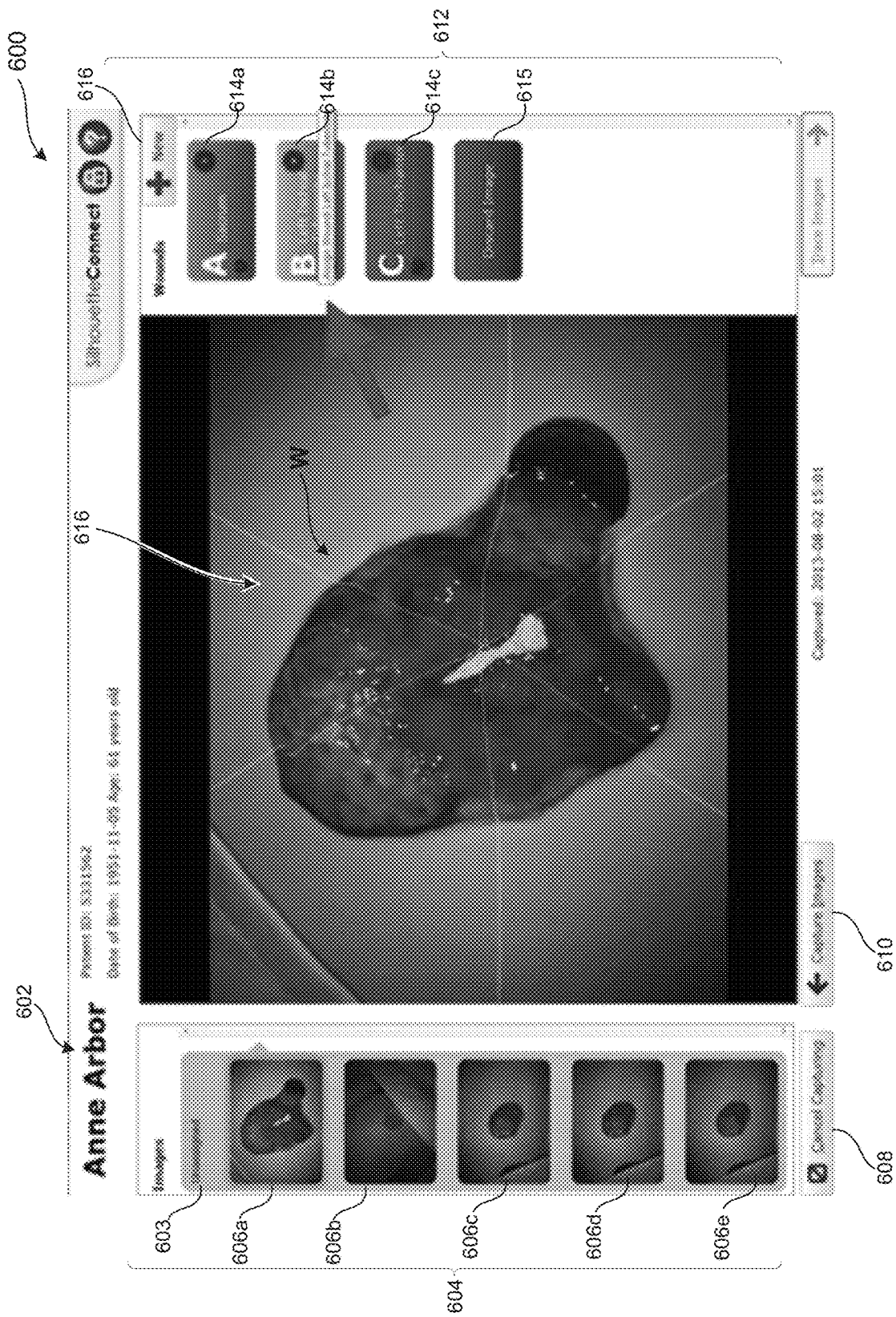
FIG. 6 is a display diagram showing a sample display typically presented by the facility to display one or more captured images and enable the user to assign a new image to a pre-existing wound.

In some embodiments (not shown), the wound information display 500 includes a button that, when selected by the user, causes a live image from the capture device 102 (FIG. 1) to be displayed on the interface module. For example, should the personal computing device 104 also be present at the point-of-care, the user may utilize the display of the personal computing device 104 to properly position the capture device 102 from the wound. In other embodiments, the capture device 102 has a display and/or the facility does not display a live image of the wound on the personal computing device 104 during image capture. The facility may further include a button (not shown) on the image capture display (not shown) that, once the user is finished capturing wound data, the user may select the button to begin assigning the captured images (containing the image data and the depth data) to the corresponding wound profile. For example, FIG. 6 is a display diagram showing a sample display 600 typically presented by the facility to display one or more captured images and enable the user to assign newly-captured wound data with a pre-existing wound. As shown in FIG. 6, the display 600 includes a new image area 604, a wound identifier area 612 having buttons 614 (similar to buttons 506a-506c in FIG. 5A), an image area 616, and a trace button 618. The new image area 604 includes an "unassigned" area 603 having buttons 606a-606e, each of which correspond to a new or unassigned image. Each of the buttons 606a-606e may include a small, preview image of the captured image so that the user can easily distinguish between the new images. To assign a new image to a wound profile, the user may drag and drop the button 606a-606e over the corresponding button 614a-c in the wound area. The facility also displays a discard button 615 for the user to remove unwanted images.

Figure 7:
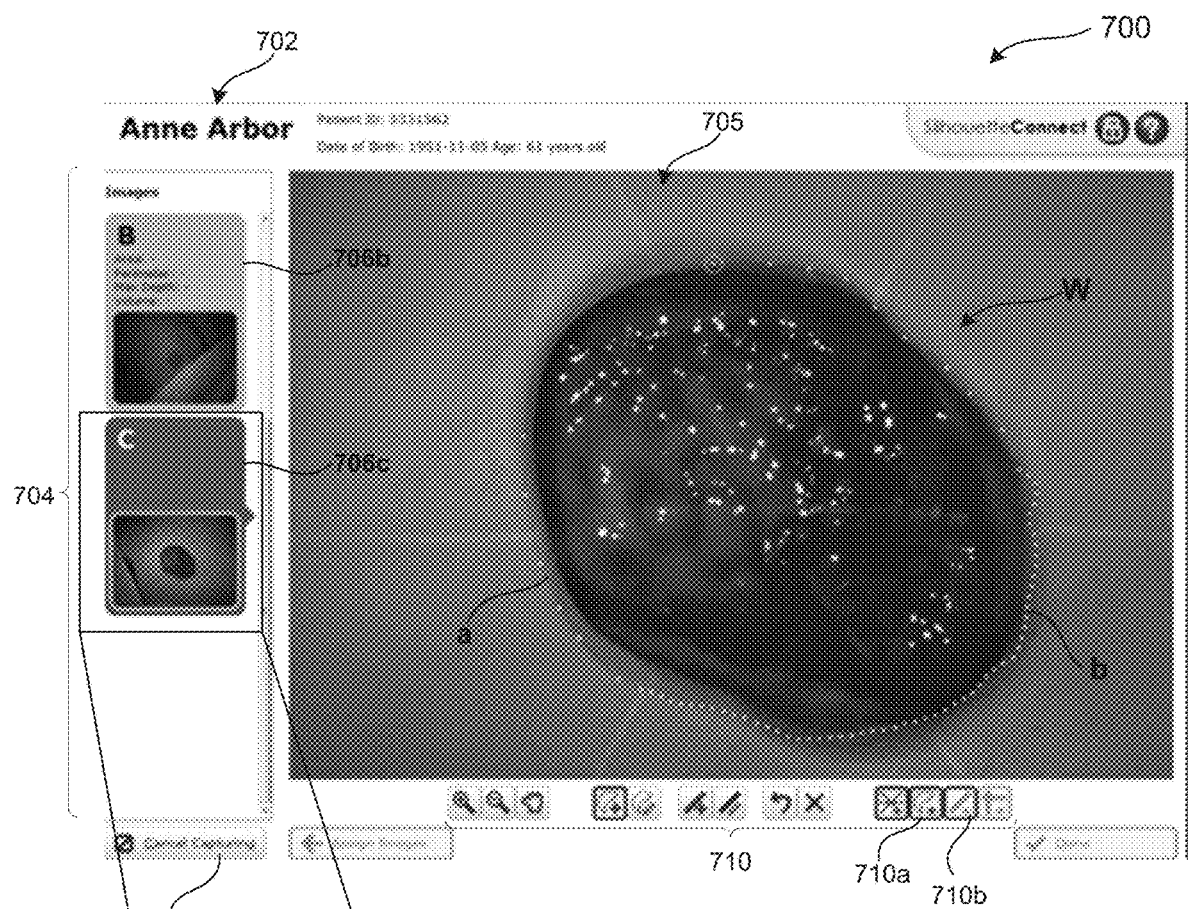
FIG. 7 is a display diagram showing a sample display typically presented by the facility to display a captured image of a surface feature and enable the user to outline the perimeter of the surface feature within the captured image.

Once the captured data has been assigned to a corresponding wound profile, the user may select the trace button 618, which causes the facility to display an interface that solicits the user to manually trace the outline of the wound. In certain embodiments, the facility utilizes image processing techniques to automatically determine an outline or outline of the wound. In such embodiments, the facility may nevertheless solicit the user to view and edit the automatically generated outline. FIG. 7, for example, is a display diagram showing a sample display 700 typically presented by the facility to display a captured image of a wound W and solicit the user to outline the outline of the wound within the captured image. The display 700 includes an image identifier area 704 and an editing area 705. The identifier area includes buttons 706a-706c (only buttons 706b and 706c shown in FIG. 7) that identify the image (with a preview image) and wound (e.g., by color and/or by reference letters "B" and "C" that correspond to a particular wound profile). When a user selects a button 706a-706c, an enlarged view of the image appears in the editing area 705. The editing area 705 includes editing buttons 710 that enable the user to edit or manipulate the image. Button 710a, for example, enables the user to click various points around the outline of the wound W, and the facility automatically displays a line (line "a") connecting the points. Button 710b enables the user to draw a continuous line (line "b") around the outline of the wound W. As shown in FIG. 7, the resulting outline line can be a combination of one or both techniques. In other embodiments, the facility may include other editing techniques. For example, in a particular embodiment, the facility may display a suggested outline line for the user and one or more buttons for adjusting the automatically generated line.

Figure 8:
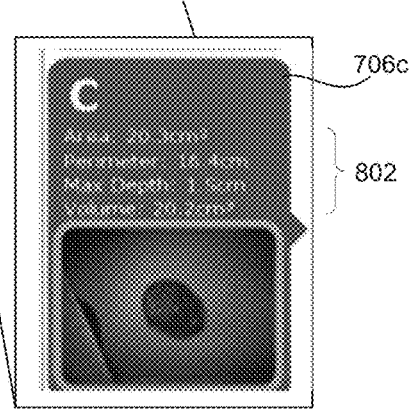
FIG. 8 is a display diagram showing a portion of the display shown in FIG. 7 after the facility has determined one or more measurements characterizing the surface feature and has displayed those measurements to the user.

Once the outline data is generated (either automatically by the facility, manually by the user's input, or a combination of both), the facility then utilizes the captured data (image data and depth data) and the outline data to determine one or more wound measurements, which in some embodiments may include generating a three-dimensional model of the wound. The facility may then update the corresponding wound identifier button 706a-706c to display the determined wound measurements. FIG. 8, for example, is a display diagram showing an enlarged view of the button 706c shown in the display 700 of FIG. 7 after being updated to include the newly determined wound measurements 802.

Figure 9:
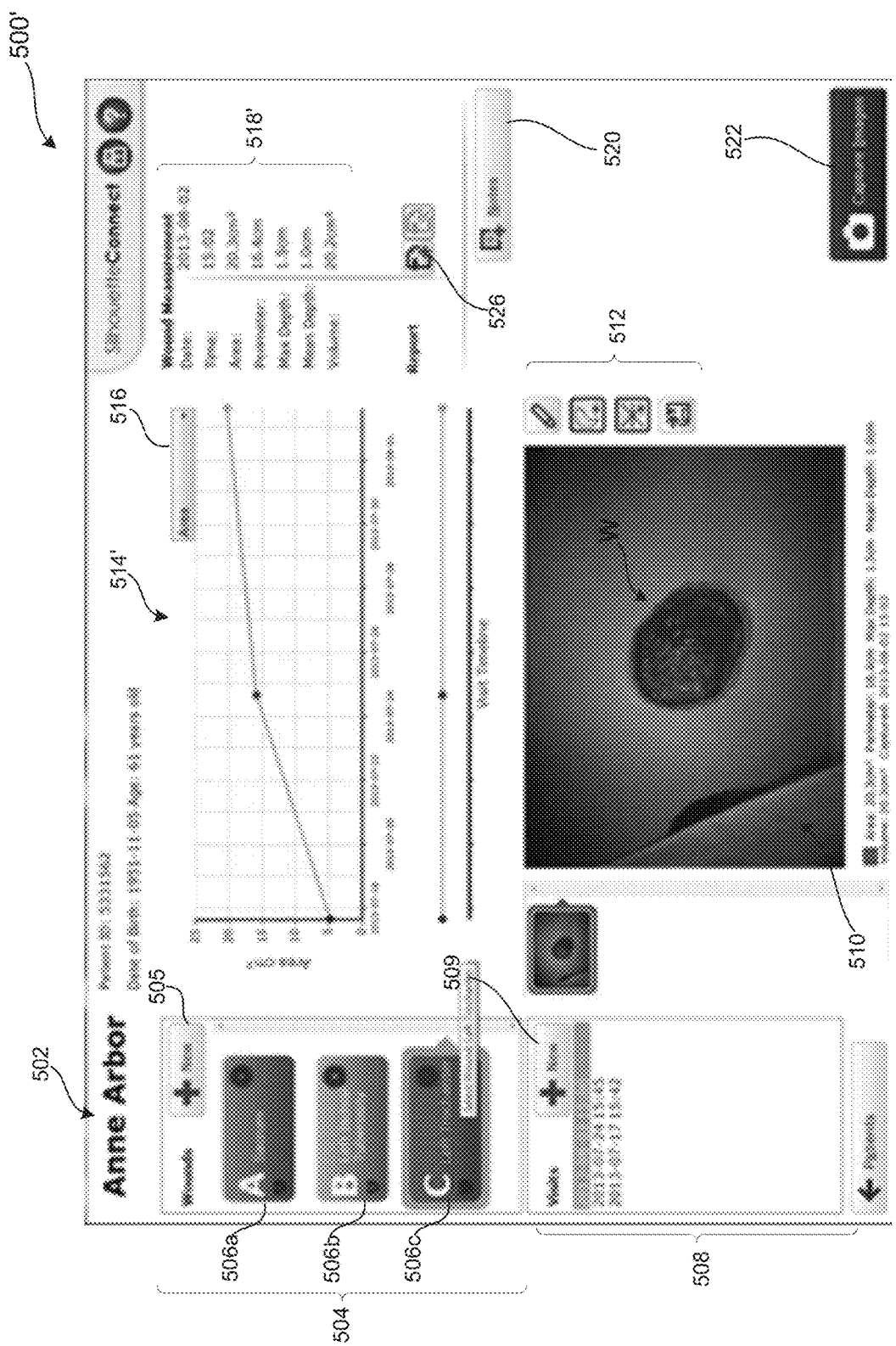
FIG. 9 is a display diagram showing a sample display typically presented by the facility to present an updated surface feature assessment for a selected patient.
Figure 10A:
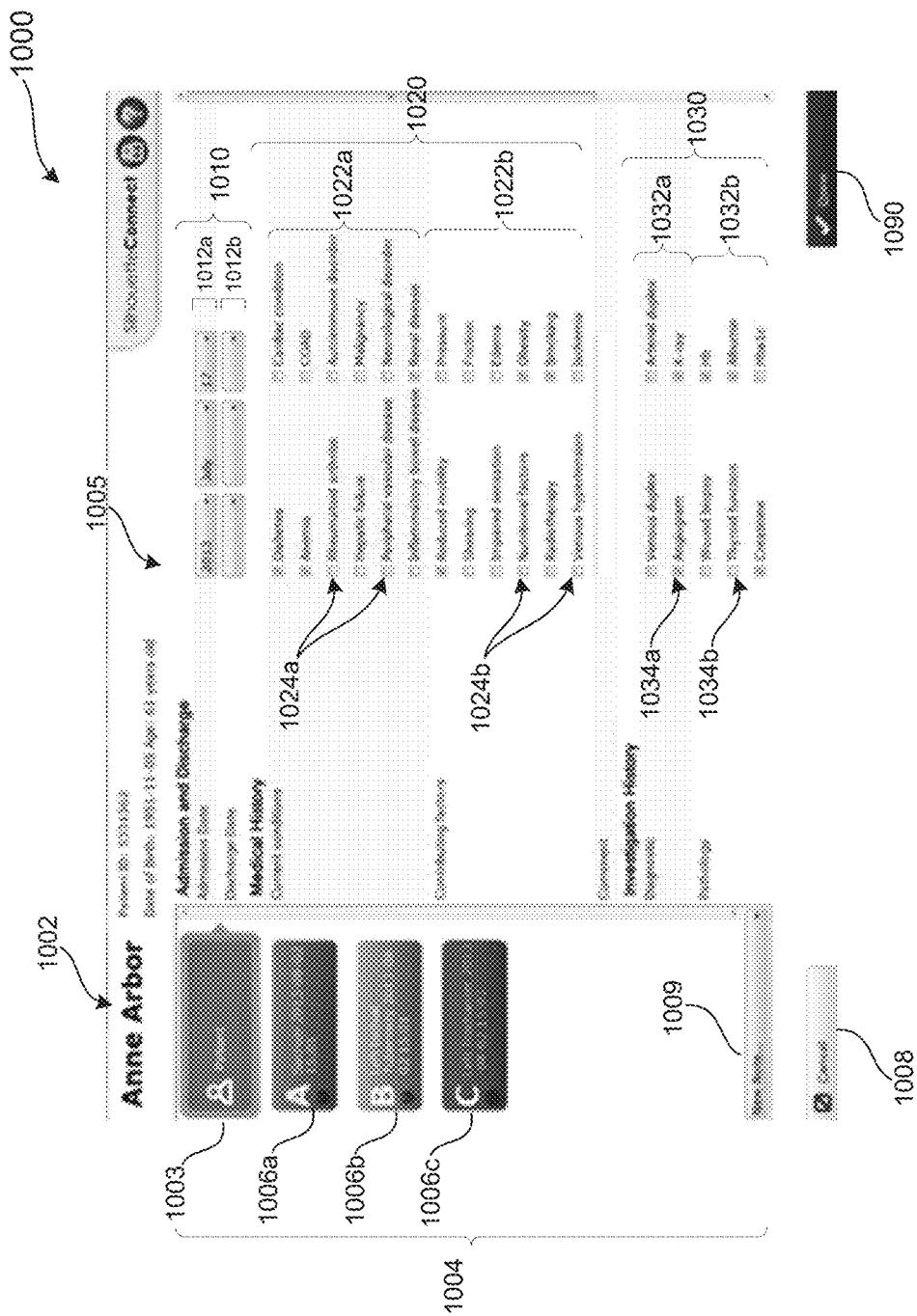
FIGS. 10A-10D are display diagrams showing sample displays typically presented by the facility to enable the user to provide notes characterizing the surface feature.
Figure 10B:
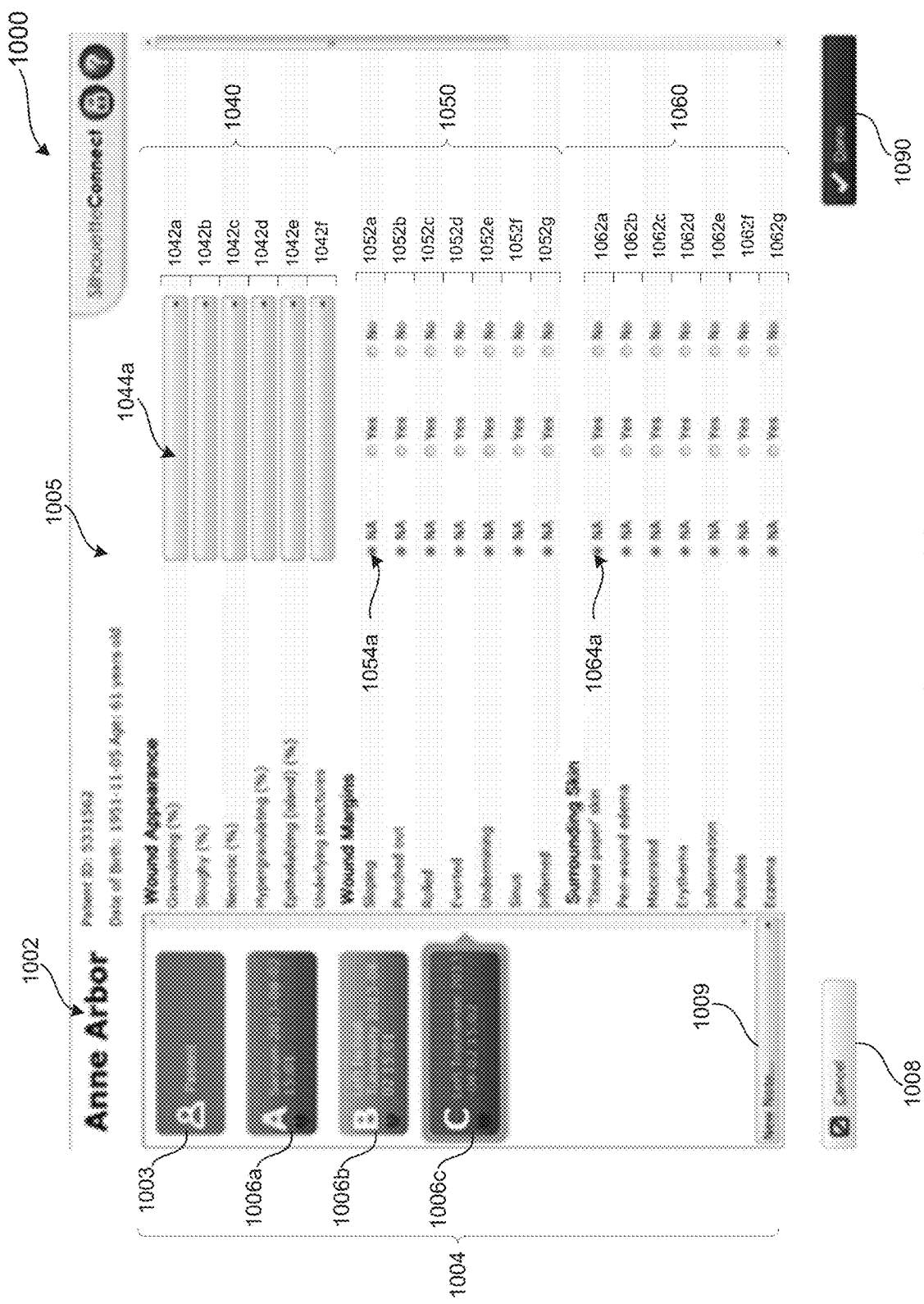
Figure 10C:
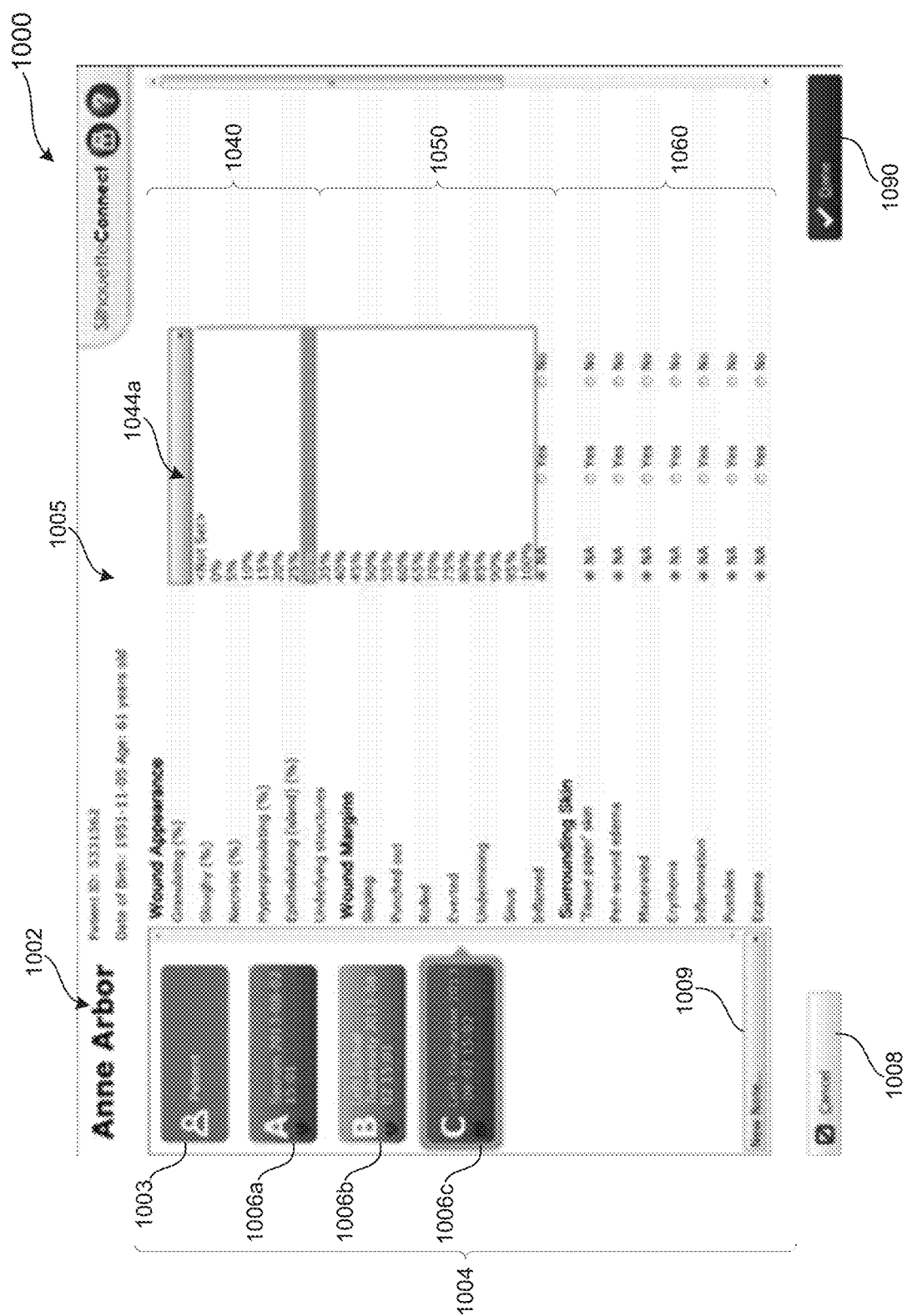
Figure 10D:
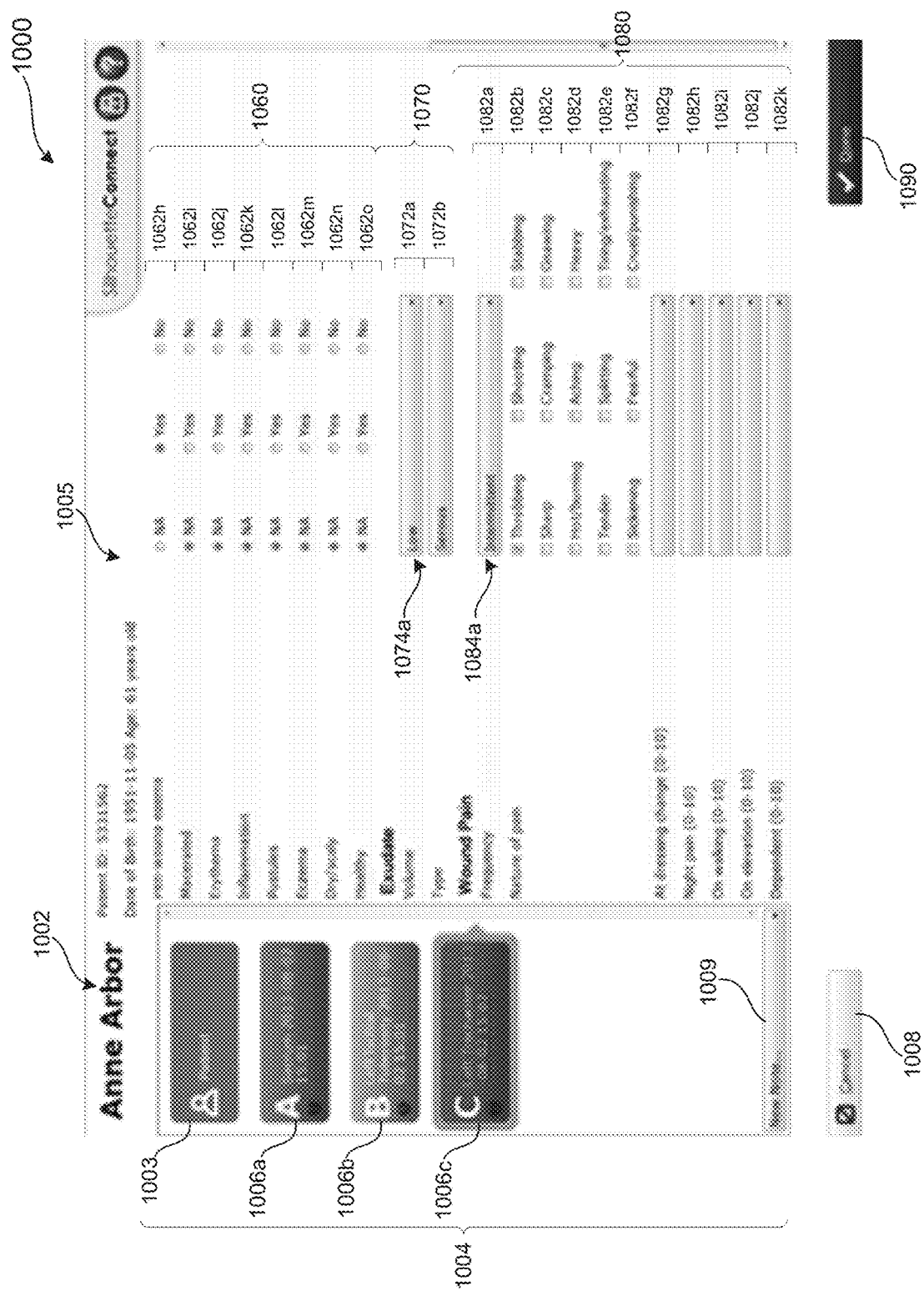

FIG. 9 is an updated version 500' of the sample wound information display 500 (FIG. 5A) after the facility has updated the measurement area 518', image area 510', and analytics area 514' to include the new capture data, outline data, and wound measurements. Updated graph 514', for example, includes an additional data point (as compared to the graph of FIG. 5A).

The facility may optionally include a button 520 that enables the user to enter additional notes characterizing a wound and/or the patient. For example, FIGS. 10A-10D are display diagrams showing a sample display 1000 presented by the facility to the user when the user selects button 520. The display 1000 includes an identifier area 1004 having a patient button 1003 and wound identifier buttons 1006a-c (similar to buttons 506a-c), and a notation area 1005. After selecting any of the patient buttons 1003 and wound identifier buttons 1006a-c, the facility displays a notation area 1005 solicits the user for input regarding the selected patient and/or wound. Display 1000 shows a sample notation area 1005 after the user has selected the patient button 1003. As shown in FIGS. 10A-10D, the notation area 1005 can include various topic areas 1010, 1020, 1030, 1040, 1050, 1060, 1070, and 1080 (referred to collectively as "topic areas 1010-1080"), such as admission and discharge, medical history, investigation history, wound appearance, wound margins, surrounding skin, exudate, and wound pain. It will be appreciated that the facility may display more or fewer notation topics. The facility may divide each of the topic areas 1010-1080 into one or more sub-topics (the sub-topics for topic area 1020 are labeled 1022a, 1022b, etc.), and each of the sub-topics may include one or more input options (the input options for sub-topic 1022a are labeled 1024a, etc.). In some embodiments, the facility may include a text field (not shown) that enables the user to enter personalized notes. When the user is finished, the user may select the "done" button 1090 to return to the updated wound information display 500' (FIG. 9).

Figure 11:
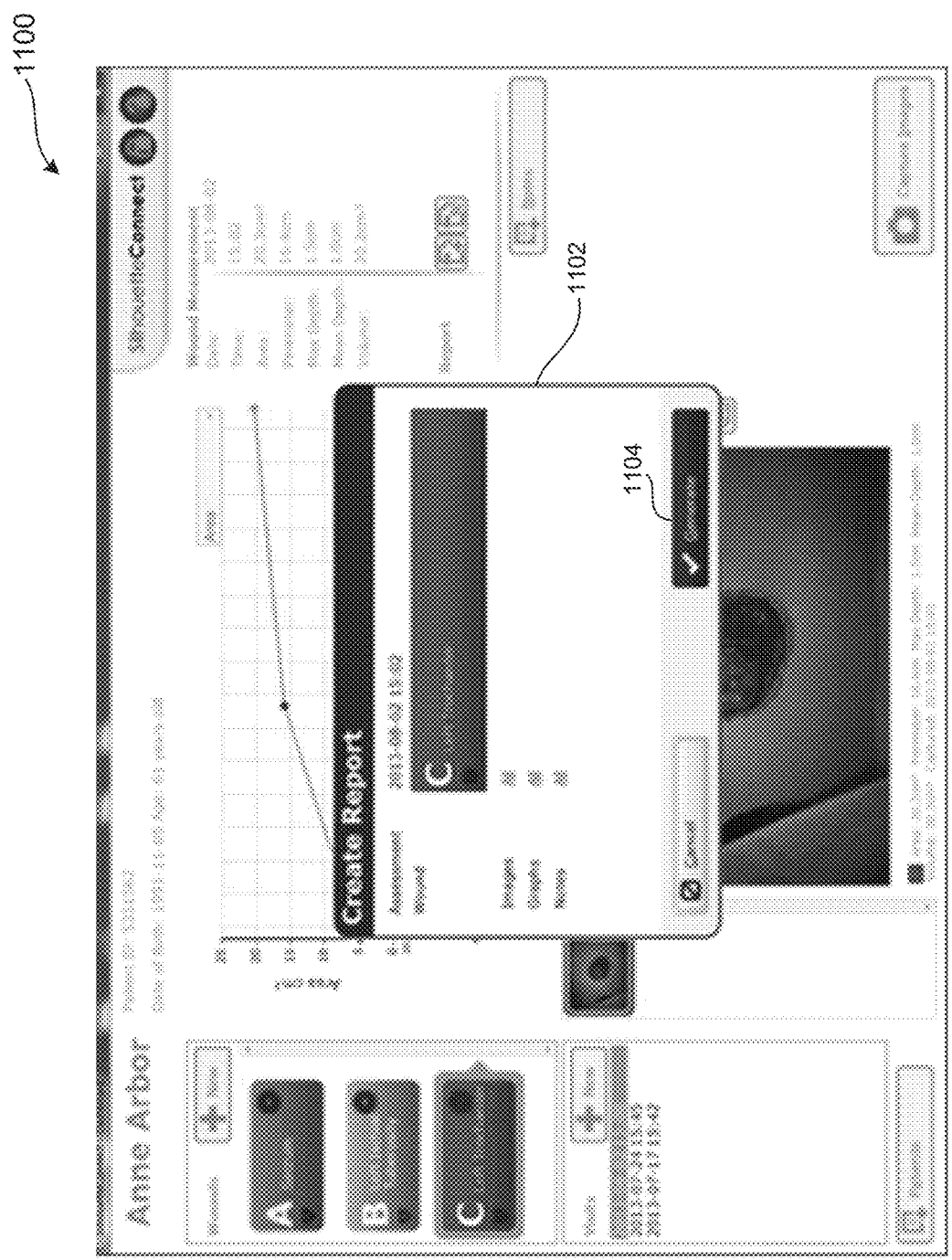
FIG. 11 is a display diagram showing a sample display typically presented by the facility when the user selects the create report button.
Figure 12A:
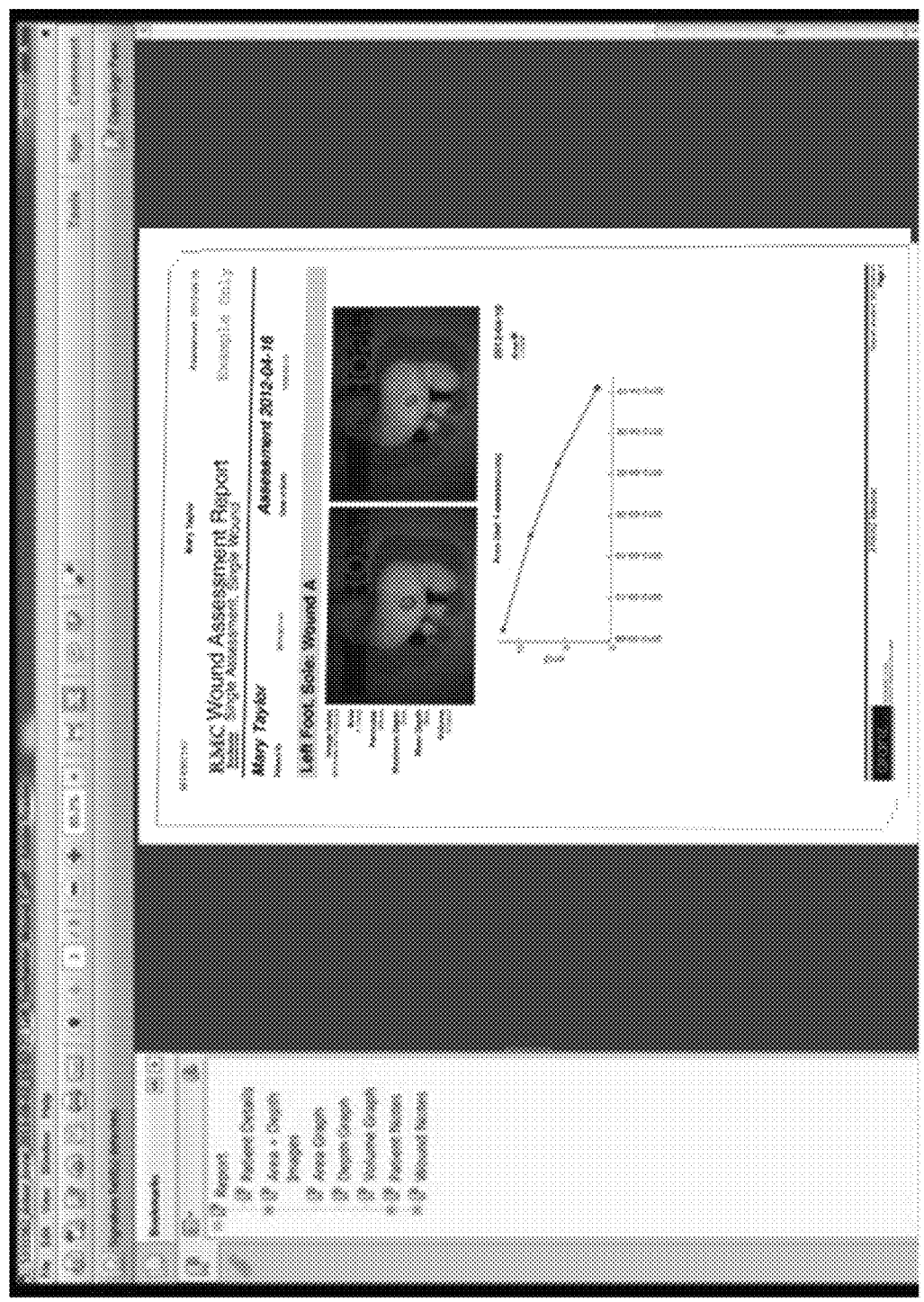
FIGS. 12A-12D are display diagrams showing a sample display typically presented by the facility to display a report characterizing the surface feature.
Figure 12B:
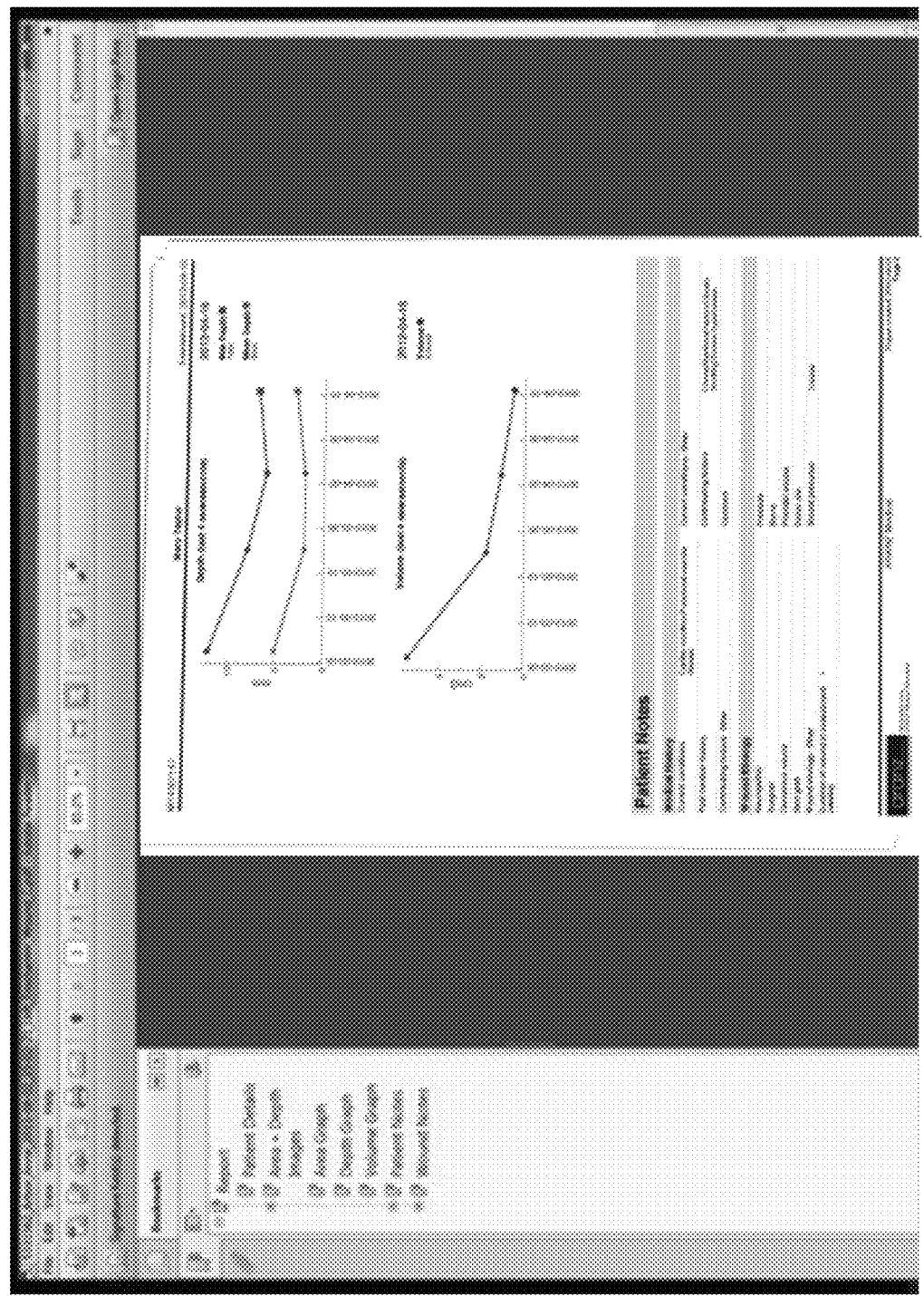
Figure 12C:
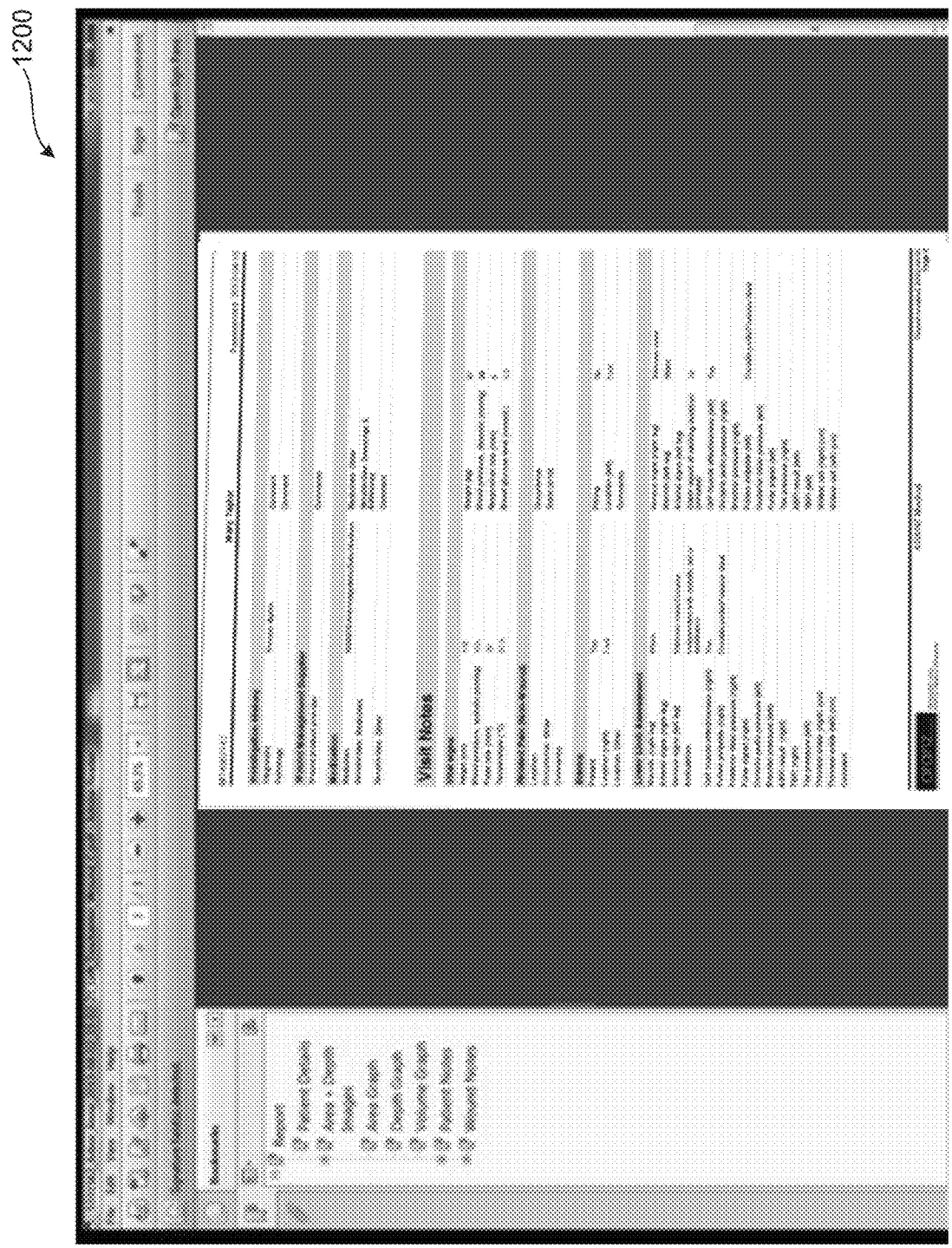
Figure 12D:
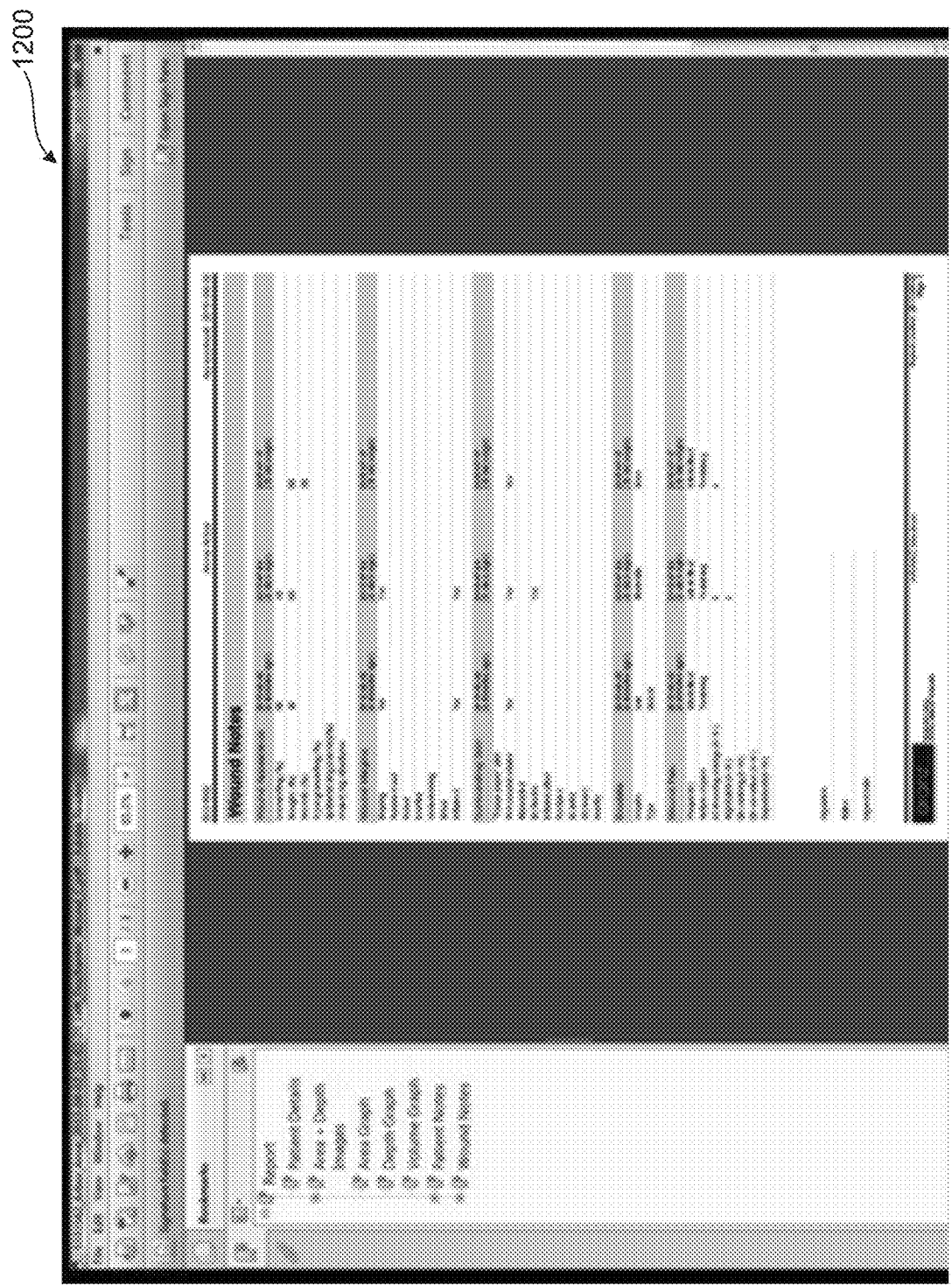

The facility also enables the user to generate a report one or more of the wounds, or the patient, generally. For example, FIG. 11 is a display diagram showing a sample display 1100 typically presented by the facility when the user selects the "create report" 526 button on the wound information display 500, 500', and FIGS. 12A-12D, for example, are display diagrams showing a sample display 1200 typically presented by the facility to display the generated report.

Although the facility is described above as providing the user a means of interacting by displaying one or more selectable buttons, it will be appreciated that other means of interacting with or controlling the facility, personal computing device, and/or capture device are within the scope of the present technology. For example, in some embodiments, in addition to or in place of any of the buttons described above, the user may interact with the facility with audio (via a microphone) and/or tactile commands (e.g., a foot control, etc.).

In those embodiments of capture devices 102 having a plurality of structured light elements (such as lasers), the capture device 102 may be configured to capture data based on a predetermined capture sequence (for example, instructions executed by the computing device 116 (FIG. 1)). An example capture sequence utilized by the capture device 102 starts with an RGB (or texture) frame captured while the light source 114 (FIG. 1) emits light. The RGB frame is followed by capture of individual frames for each structured light element (a frame is captured while each structured light element is turned on by itself), as well as a frame for the combination of structured light elements. During capture of the RGB frame, the structured light elements 112 do not emit light. Likewise, during capture of the structured light frames, the light source 114 does not emit light. However, post-capture processing methods require that only one type of light source (regardless of the number of light sources per type) is enabled during the capture sequence. Existing imaging devices meet this requirement by configuring the image sensor to operate in a "single frame capture mode" (i.e., pauses are inserted between consecutive frames of the capture sequence). However, because of the added pauses, "single frame capture mode" results in an increase in total capture time. To address this shortcoming, the image sensor 110 may be configured to operate in video mode (continuous streaming) which reduce capture times because it eliminates the pauses and "pipelines" the imaging processing steps. Suitable image sensors that operate in video mode include, for example, a 5-megapixel Omnivision OV5640 image sensor. Such image sensors, however, often utilize a rolling shutter (i.e., only a fraction of the sensor rows are exposed to light at any instant). For some of the image sensors that utilize a rolling shutter, the end the current frame and the beginning of the next frame overlap, and thus two disjoint fractions of the sensor rows are exposed to light at the same instant. This overlap results in cross-talk between successive frames. To avoid the potential for such cross-talk to reduce the utility of the captured frames, a specific capture sequence is employed and one or more multiplicative binary masks are applied to the structured light frames that reject the cross-talk from the previous frame (and also the next frame in cases where illumination for the next frame is pre-enabled) and also range gate the laser returns to certain depths (e.g., between 200 mm and 350 mm). In these and other embodiments, the image sensor 110 may additionally or alternatively be configured to operate in a "single frame capture mode." Additionally, because the capture device 102 is a handheld device and relative motion inevitably occurs between the capture device 102 and the patient over the course of the capture sequence, the facility and/or capture device 102 of the present technology may include one or more motion compensation algorithms to reduce or eliminate the negative effect of such motion on the resulting image and/or data quality.

Conclusion

It will be appreciated by those skilled in the art that the above-described facility may be straightforwardly adapted or extended in various ways. For example, the facility may use a variety of user interfaces to collect various information usable in determining valuations from users and other people knowledgeable about homes, and a variety of user interfaces to display refined valuations. While the foregoing description makes reference to particular embodiments, the scope of the invention is defined solely by the claims that follow and the elements recited therein.

While computing devices configured as described above are typically used to support the operation of the facility, one of ordinary skill in the art will appreciate that the facility may be implemented using devices of various types and configurations, and having various components. For example, in some instances the capture devices 102 and the personal computing devices 104 may communicate directly with each other (in addition to communicating with the server computer 106) through a wired or wireless connection. Such a configuration could provide the user a live image of the wound faster and/or provide a higher quality live preview image. In such embodiments, suitable restrictions can be administered when sending and storing patient data to ensure confidentiality. In another variation, the capture device 102 is only in communication (wired or wirelessly) with the computing device 104, and the computing device 104 communicates with the server computer 106 (e.g., via cellular data protocols), thereby serving as a pass through for patient data without permanently storing the patient data. In yet another variation, the facility may route communications from the capture devices 102 and the computing devices 104 through a common access point, rather than the two separate access points (first and second access points 140, 142) shown in FIG. 1. Additionally, the facility may provide the user with audit information for the assessments (e.g., who performed the assessments, who accessed the assessments, etc.).

Although not required, aspects of the present technology have been described in the general context of computer-executable instructions, such as routines executed by a general-purpose computer, a personal computer, a server, or other computing system. The present technology can also be embodied in a special purpose computer or data processor that is specifically programmed, configured, or constructed to perform one or more of the computer-executable instructions explained in detail herein.

We claim:

1. A computer-implemented method for evaluating one or more anatomical surface features ("surface features") of a patient, the method comprising:
   receiving, at a non-volatile storage device, two or more data sets, each data set characterizing one of the one or more surface features, wherein each of the two or more data sets is generated at and received from a remote data capture device;
   storing the two or more data sets in a patient profile at the non-volatile storage device;
   receiving user instructions assigning a first data set of the two or more data sets to a first surface feature profile associated with a first surface feature of the one or more surface features;
   storing the first data set in the first surface feature profile;
   determining, based on the first data set, one or more first surface feature measurements;
   storing, at the non-volatile storage device, the determined one or more first surface feature measurements; and
   displaying one or more of the determined one or more first surface feature measurements on a web-based interface.

2. The method of claim 1, further comprising:
   receiving user instructions assigning a second data set of the two or more data sets to a second surface feature profile associated with a second surface feature of the one or more surface features;
   storing the second data set in the second surface feature profile;
   determining, based on the second data set, one or more second surface feature measurements;
   storing, at the non-volatile storage device, the determined one or more second surface feature measurements; and
   displaying one or more of the determined one or more second surface feature measurements on the web-based interface.

3. The method of claim 1, further comprising receiving the user instructions assigning the first data set via the web-based interface.

4. The method of claim 1, further comprising, after capture of the two or more data sets, displaying a representation of each of the two or more data sets to a user via the web-based interface.

5. The method of claim 1 wherein the user instructions assigning the first data set comprise a user dragging a representation of the first data set into a wound area on the web-based interface.

6. The method of claim 5 wherein the representation of the first data set includes a preview image based on a captured image of the first data set.

7. The method of claim 1 wherein none of the two or more data sets, or the determined one or more first surface feature measurements, are stored in a non-volatile memory of the data capture device.

8. The method of claim 1, wherein the one or more first surface feature measurements include an area of the first surface feature and a volume of the first surface feature.

9. The method of claim 1 wherein the first data set includes (a) image data characterizing the first surface feature and (b) depth data characterizing a depth of the first surface feature, and wherein the method further includes automatically determining an outline of the first surface feature based on the raw data.

10. The method of claim 1, further comprising obtaining, at the web-based interface, user input identifying an outline of the first surface feature.

11. The method of claim 1, further comprising obtaining, at the web-based interface, user input characterizing the surface feature and storing, at the non-volatile storage device, the user input.

12. A non-transitory computer-readable storage medium encoded with instructions that, when executed by a processor, causes the processor to perform a method for evaluating an anatomical surface feature ("surface feature"), the method comprising:
receiving, at a server computer, two or more data sets, each data set characterizing one of the one or more surface features, wherein each of the two or more data sets is generated at and received from a remote data capture device;
storing the two or more data sets in a patient profile at a non-volatile memory of the server computer,
receiving user instructions assigning a first data set of the two or more data sets to a first surface feature profile associated with a first surface feature of the one or more surface features;
storing the first data set in the first surface feature profile at a non-volatile memory of the server computer;
with a processor at the server computer, determining, based on the first data set, one or more first surface feature measurements;
storing, at a non-volatile memory of the server computer, the determined one or more first surface feature measurements; and
displaying one or more of the determined one or more first surface feature measurements on a web-based interface.

13. The non-transitory computer-readable storage medium of claim 12, the method further comprising:
receiving user instructions assigning a second data set of the two or more data sets to a second surface feature profile associated with a second surface feature of the one or more surface features;
storing the second data set in the second surface feature profile;
determining, based on the second data set, one or more second surface feature measurements;
storing, at the non-volatile storage device, the determined one or more second surface feature measurements; and
displaying one or more of the determined one or more second surface feature measurements on the web-based interface.

14. The non-transitory computer-readable storage medium of claim 12, the method further comprising receiving the user instructions assigning the first data set via the web-based interface.

15. The non-transitory computer-readable storage medium of claim 12, the method further comprising, after capture of the two or more data sets, displaying a representation of each of the two or more data sets to a user via the web-based interface.

16. The non-transitory computer-readable storage medium of claim 12, wherein the user instructions assigning the first data set comprise a user dragging a representation of the first data set into a wound area on the web-based interface.

17. The non-transitory computer-readable storage medium of claim 16, wherein the representation of the first data set includes a preview image based on a captured image of the first data set.

18. The non-transitory computer-readable storage medium of claim 12, wherein none of the two or more data sets, or the determined one or more first surface feature measurements, are stored in a non-volatile memory of the data capture device.

19. The non-transitory computer-readable storage medium of claim 12, wherein the one or more first surface feature measurements include an area of the first surface feature and a volume of the first surface feature.

20. The non-transitory computer-readable storage medium of claim 12, wherein the first data set includes (a) image data characterizing the first surface feature and (b) depth data characterizing a depth of the first surface feature, and wherein the method further includes automatically determining an outline of the first surface feature based on the raw data.

21. The non-transitory computer-readable storage medium of claim 12, further comprising obtaining, at the web-based interface, user input identifying an outline of the first surface feature.

22. The non-transitory computer-readable storage medium of claim 12, further comprising obtaining, at the web-based interface, user input characterizing the surface feature and storing, at the non-volatile storage device, the user input.

* * * * *